US009922164B2

(12) United States Patent
Chennamsetty et al.

(10) Patent No.: US 9,922,164 B2
(45) Date of Patent: Mar. 20, 2018

(54) METHODS TO IDENTIFY MACROMOLECULE BINDING AND AGGREGATION PRONE REGIONS IN PROTEINS AND USES THEREFOR

(71) Applicants: Novartis AG, Basel (CH); Massachusetts Institute of Technology, Cambridge, MA (US)

(72) Inventors: Naresh Chennamsetty, Cambridge, MA (US); Bernhard Helk, Basel (CH); Bernhardt Trout, Cambridge, MA (US); Veysel Kayser, Cambridge, MA (US); Vladimir Voynov, Cambridge, MA (US)

(73) Assignees: Novartis AG, Basel (CH); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/249,161

(22) Filed: Aug. 26, 2016

(65) Prior Publication Data

US 2016/0364521 A1     Dec. 15, 2016

Related U.S. Application Data

(62) Division of application No. 13/000,353, filed as application No. PCT/US2009/047954 on Jun. 19, 2009, now abandoned.

(60) Provisional application No. 61/074,466, filed on Jun. 20, 2008.

(51) Int. Cl.
| | |
|---|---|
| *G06F 19/16* | (2011.01) |
| *C07K 14/71* | (2006.01) |
| *C07K 16/00* | (2006.01) |
| *G06F 19/24* | (2011.01) |
| *G06F 19/00* | (2018.01) |
| *A61K 38/00* | (2006.01) |

(52) U.S. Cl.
CPC .............. *G06F 19/16* (2013.01); *C07K 14/71* (2013.01); *C07K 16/00* (2013.01); *A61K 38/00* (2013.01); *C07K 2317/94* (2013.01); *G06F 19/24* (2013.01); *G06F 19/70* (2013.01)

(58) Field of Classification Search
None
See application file for complete search history.

(56) References Cited

U.S. PATENT DOCUMENTS

| 6,277,375 | B1 | 8/2001 | Ward |
| 8,747,848 | B2 | 6/2014 | Chennamsetty et al. |
| 2002/0103212 | A1 | 8/2002 | Serizawa et al. |
| 2005/0244403 | A1 | 11/2005 | Lazar et al. |
| 2006/0271306 | A1* | 11/2006 | Dobson .................. G06F 19/16 |
| | | | 702/19 |
| 2007/0092940 | A1 | 4/2007 | Eigenbrot et al. |
| 2007/0202098 | A1 | 8/2007 | Lazar et al. |
| 2008/0050310 | A1 | 2/2008 | Ebens |
| 2010/0297103 | A1 | 11/2010 | Murakami |
| 2013/0053547 | A1 | 2/2013 | Kai et al. |

FOREIGN PATENT DOCUMENTS

| CN | 1671741 A | 9/2005 |
| CN | 1958615 A | 5/2007 |
| EP | 1810979 A1 | 7/2007 |
| EP | 2006380 A1 | 12/2008 |
| JP | 2003-263465 A | 9/2003 |
| WO | WO-2003/074679 A2 | 9/2003 |
| WO | WO-2004/001007 A2 | 12/2003 |
| WO | WO-2005/045442 A1 | 5/2005 |
| WO | WO-2006/034488 A2 | 3/2006 |
| WO | WO-2006033386 A1 | 3/2006 |
| WO | WO-2007/022070 A2 | 2/2007 |
| WO | WO-2007/103288 A2 | 9/2007 |
| WO | WO-2007/109221 A2 | 9/2007 |
| WO | WO-2008/032833 A1 | 3/2008 |
| WO | WO-2008/088983 A1 | 7/2008 |

OTHER PUBLICATIONS

Abraham et al. (1987). "Extension of the fragment method to calculate amino acid zwitterion and side chain partition coefficients," Proteins: Structure, function, and genetics 130-152, p. 148.
Black et al. (1991). "Development of hydrophobicity parameters to analyze proteins which bear post- or cotranslational modifications," Anal Biochem 193:72-82.
Brard et al. (Sep. 6, 1999) "Somatic mutation and light chain rearrangement generate autoimmunity in anti-single-stranded DNA transgenic MRUlpr mice" Journal of Experimental Medicine 190(5):691-704.
Burgess et al. (1990). "Possible dissociation of the heparin-binding and mitogenic activities of heparin-binding (acidic fibroblast) growth factor-1 from its receptor-binding activities by site-directed mutagenesis of a single lysine residue," J Cell Biol 111:2129-2138.
Cellmer et al. (May 17, 2007). "Protein aggregation in silico," Trends in Biotechnology 25(6):254-257.
Chennamsetty et al. (Aug. 14, 2009). "Aggregation-prone motifs in human immunoglobulin G" J Mol Biol 391(2):404-413.

(Continued)

*Primary Examiner* — Michael Borin
(74) *Attorney, Agent, or Firm* — Morrison & Foerster LLP

(57) ABSTRACT

The present invention provides methods and computational tools based, at least in part, on computer simulations that identify macromolecule binding regions and aggregation prone regions of a protein. Substitutions may then be made in these aggregation prone regions to engineer proteins with enhanced stability and/or a reduced propensity for aggregation. Similarly, substitutions may then be made in these macromolecule binding regions to engineer proteins with altered binding affinity for the macromolecule.

8 Claims, No Drawings

(56) References Cited

OTHER PUBLICATIONS

Chennamsetty, N. et al. (Jul. 2009). "Design of therapeutic proteins with enhanced stability," *Proceedings of the National Academy of Sciences of the United States of America* 106(29):11937-11942.
Connolly (1983). "Solvent-accessible surfaces of proteins and nucleic acids," Science. 221(4612):709-13.
De Groot, N.S. et al. (Sep. 30, 2005). "Prediction of hot spots of aggregation in disease-linked polypeptides," *BMC Structural Biology* 5(1):18.
Gokarn et al. (2008). "Self-buffering antibody formulations," J Pharma Sci 97:3051-3066.
Hou et al. (2005). "An extended aqueous solvation model based on atom-weighted solvent accessible surface areas: SAWSA v2.0 model," J Mol Model 11(1):26-40.
Hsu (1994). "The variation in immunoglobulin heavy chain constant regions in evolution," Semin Immunol. 6(6):383-91.
International Preliminary Report on Patentability dated Feb. 12, 2013, for PCT/US2009/047948, 13 pages.
International Search Report and Written Opinion dated Jan. 25, 2013, for PCT/US2009/047948, 23 pages.
International Search Report and Written Opinion dated Nov. 30, 2009, for PCT Application No. PCT/US2009/047954 filed Jun. 19, 2009, 20 pages.
International search report dated Jan. 12, 2011, for PCT/US2010/037517 filed Jun. 4, 2010, 8 pages.
Ivanov A.S. et al. (2002). "Computer aided drug design based on structure of macromolecular target: I. Search and description of ligand binding sites in target protein," Problems of medical chemistry, 48(3): 304-315 (article in Russian).
Jespers et al. (2004) "Aggregation-resistant domain antibodies selected on phage by heat denaturation," Nature Biotech 22:1161-1165.
Junutula et al. (Aug. 1, 2008) "Site-specific conjugation of a cytotoxic drug to an antibody improves the therapeutic index" Nature Biotechnology 26(8):925-932.
Junutula et al. (Jan. 14, 2008). "Rapid identification of reactive cysteine residues for site-specific labeling of antibody-Fabs" Journal of Immunological Methods, 332(1-2):41-52.
Kellog et al. (1991). "HINT: a new method of empirical hydrophobic field calculation for CoMFA," J Computer-Aided Molec Des 5:545-552.
Lazar et al. (1998). "Transforming growth factor alpha: mutation of aspartic acid 47 and leucine 48 results in different biological activities," Mol Cell Biol 8:1247-1252.
Lee et al. (1971). "The interpretation of protein structures: estimation of static accessibility," J Mol Biol 55:379-400.
Lu et al. (Feb. 2008). "The effect of a point mutation on the stability of IgG4 as monitored by analytical ultracentrifugation," J Pharma Sci 97(2):960-969.
Lyons et al. (Jan. 1, 1990) "Site-specific attachment to recombinant antibodies via introduced surface cysteine residues" Protein Engineering 3(8):703-708.
Nelson et al. (2000). Principles of Biochemistry, p. 1-1152.
Nieba et al. (1997). "Disrupting the hydrophobic patches at the antibody variable/constant domain interface: improved in vivo folding and physical characterization of an engineered scFv fragment," Protein Eng. 10(4):435-44.
Partial European Search Report dated Jun. 11, 2015 for EP15156284.0, 8 pages.
Patro et al. (1994)." Simulations of kinetically irreversible protein aggregate structure," Biophys J. 66(5):1274-89.
Pawar, A.P. et al. (Jul. 8, 2005). "Prediction of 'Aggregate-prone' and 'Aggregate-susceptible' Regions in Proteins Associated with Neurodegenerative Diseases," *Journal of Molecular Biology* 350(2):379-392.
Putnam et al. (1981). "Amino acid sequence of the first constant region domain and the hinge region of the delta heavy chain of human IgD," Proc Natl Acad Sci U S A. 78(10):6168-72.
Raschke et al. (2001). "Quantification of the hydrophobic interaction by simulations of the aggregation of small hydrophobic solutes in water," Proc Natl Acad Sci U S A. 98(11):5965-9.
Russian Decision to Grant, for Russian Application No. 2011101997/10, filed Jun. 19, 2009, Decision dated Jul. 8, 2015, 20 pages (10 pages translation and 10 pages Russian Decision).
Spassov, V. et al. (1995). "The optimization of protein-solvent interactions: Thermostability and the role of hydrophobic and electrostatic interactions," *Protein Science* 4(8):1516-1527.
Stimmel et al. (Sep. 29, 2000) "Site-specific conjugation on serine-cysteine variant monoclonal antibodies" Journal of Biological Chemistry 275(39):30445-30450.
Thermo Scientific (2003). "Antibody Structure and Classes of Immunoglobulins," 4 pages. Retrieved May 3, 2013 from <http://www.piercenet.com/browse.cfm?fldID=F6556788-5056-8A76-4EAC-3683B8E3197A>.
Voynov et al. (Feb. 17, 2010) "Design and application of antibody cysteine variants." Bioconjugate Chemistry 21(2):385-392.
Wesson et al. (1992). "Atomic solvation parameters applied to molecular dynamics of proteins in solution," Protein Sci 1(2):227-235.

* cited by examiner

METHODS TO IDENTIFY MACROMOLECULE BINDING AND AGGREGATION PRONE REGIONS IN PROTEINS AND USES THEREFOR

CROSS-REFERENCE TO RELATED APPLICATIONS

This application is a Divisional of U.S. patent application Ser. No. 13/000,353, claiming an international filing date of Jun. 19, 2009, which is a U.S. National Phase of International Patent Application No. PCT/US2009/047954, filed Jun. 19, 2009, which claims the benefit of U.S. Provisional Patent Application No. 61/074,466, filed Jun. 20, 2008, all of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 619672000310 SeqList.txt, date recorded: Jun. 27, 2016, size: 2 KB).

BACKGROUND OF THE INVENTION

Understanding and controlling protein stability has been a coveted endeavor to Biologists, Chemists, and Engineers. The first link between amino acid substitution and disease (Ingram. Nature. 1957, 180(4581):326-8) offered a new and essential perspective on protein stability in health and disease. The recent tremendous increase of protein-based pharmaceuticals has created a new challenge. Therapeutic proteins are stored in liquid for several months at very high concentrations. The percent of non-monomeric species increases with time. As aggregates form, not only the efficacy of the product decreases, but side effects such as immunological response upon administration may occur. Assuring stability of protein pharmaceuticals for the shelf-life of the product is imperative.

Because of their potential in the cure of various diseases, antibodies currently constitute the most rapidly growing class of human therapeutics (Carter. Nature Reviews Immunology. 2006, 6(5), 343). Since 2001, their market has been growing at an average yearly growth rate of 35%, the highest rate among all categories of biotech drugs (S. Aggarwal, Nature. BioTech. 2007, 25 (10) 1097).

Therapeutic antibodies are prepared and stored in aqueous solutions at high concentrations, as required for the disease treatment. However, these antibodies are thermodynamically unstable under these conditions and degrade due to aggregation. The aggregation in turn leads to a decrease in antibody activity making the drug ineffective and can even generate an immunological response. As such, there is an urgent need to develop a mechanistic understanding of how these antibodies, and indeed proteins in general, aggregate, to discover what regions of the protein are involved in the aggregation, and to develop strategies to hinder aggregation.

These effects are particularly important to antibody therapeutics. One approach to antibody stabilization is to graft the CDR loops that confer antigen binding specificity onto a more stable framework (Ewert, Honegger, and Pluckthun, Biochemistry. 2003, 42(6): 1517-28.). This approach will only work if the amino acid sequence in the CDR loops is not the driving aggregation force, and if grafting the CDR loops onto a more stable framework does not change the antigen binding specificity.

The technology related to predicting protein aggregation prone regions can be divided into two categories, 1) Phenomenological models and 2) Molecular simulation techniques. The phenomenological models are mainly based on predicting the aggregation 'hot spots' from protein primary sequences using properties such as hydrophobicity, β-sheet propensity etc, whereas the molecular simulation techniques use the three dimensional structure and dynamics of proteins to locate the regions prone to aggregation. Most of the techniques have been directed toward understanding amyloid fibril formation and aggregation of other small proteins where β-sheet formation is predominant.

Phenomenological models have been developed based on physicochemical properties such as hydrophobicity, β-sheet propensity etc., to predict the aggregation prone regions from protein primary sequence (Caflisch, *Current Opinion in Chemical Biology.* 2006, 10, 437-444; Chiti and Dobson. Annu. Rev. Biochem. 2006, 75: 333-366). One of the initial phenomenological models was based on mutational studies of the kinetics of aggregation of a small globular protein 'Human muscle acylphosphatase (AcP) along with other unstructured peptides and natively unfolded proteins (Chiti, et al. *Nature.* 2003, 424 p. 805-808; U.S. Pat. No. 7,379, 824]. This study revealed simple correlations between aggregation and physicochemical properties such as β-sheet propensity, hydrophobicity and charge. These studies were done under conditions at which the proteins are mainly unstructured. Thus a three parameter empirical model was developed that links sequence to the aggregation propensity (Chiti, et al. Nature. 2003, 424, 805-808). This model was also used to suggest variants of the 32-residue peptide hormone calcitonin to reduce its aggregation propensity (Fowler, et al. *Proc Natl Acad Sci USA.* 2005, 102, 10105-10110.). DuBay and coworkers have extended the three-parameter equation (Chiti, et al. Nature. 2003, 424, 805-808) into a seven-parameter formula that includes intrinsic properties of the polypeptide chain and extrinsic factors related to the environment such as peptide concentration, pH value and ionic strength of the solution) (Dubay, et al. *J Mol Biol.* 2004, 341, 1317-1326). Using this model they were able to reproduce the in vitro aggregation rates of a wide range of unstructured peptides and proteins. However, the main limitation of the seven-parameter model is that all residues in the sequence were given same relative importance. This is inconsistent with experimental and simulation observation which show that certain regions are more important than others, depending on their secondary structure propensities. Recently, this analysis was further extended to include protection factors to describe the aggregation of structured polypeptide chains (Tartaglia, G. G., Pawar, A. P., Campioni, S, Dobson, C. M., Chiti, F., and Vendruscolo, M. J Mol Biol (2008) in press). Some of the predicted sites were in agreement with the known aggregation prone sites for proteins such as Lysozyme, Myoglobin, etc. A phenomenological model without free parameters was developed (Tartaglia, et al. *Protein Sci.* 2004, 13, 1939-1941; Tartaglia et al. *Protein Sci.* 2005, 14, 2723-2734) to predict changes in elongation rate of the aggregate fibril upon mutation and identify aggregation prone segments. The physicochemical properties used are the change in β-propensity upon mutation, the change in number of aromatic residues, and the change in total charge. Furthermore, the ratio of accessible surface area is taken into account if the wild-type and mutant side chains are both polar or both apolar, whereas the dipole moment of the polar side chain is used in the case of apolar to polar (or polar to apolar) mutation. This model reproduced the relative aggregation propensity of a set of 26 heptapeptide sequences, which were predicted to favor an in-register parallel β-sheet arrangement.

The model of DuBay and coworkers (Dubay et al. *J Mol Biol*. 2004, 341, 1317-1326) has been modified with the inclusion of α-helical propensity and hydrophobic patterning, and comparing the aggregation propensity score of a given amino acid sequence with an average propensity calculated for a set of sequences of similar length (Pawar, et al., *J Mol Biol*. 2005, 350, 379-392). This model has been validated on the aggregation-prone segments of three natively unfolded polypeptide chains: Aβ42, asynuclein and the tau protein.

Another algorithm called TANGO (Fernandez-Escamilla, et al., *Nat Biotechnol*. 2004, 22, 1302-1306) was developed, which balances the same physico-chemical parameters, supplemented by the assumption that an amino acid is fully buried in the aggregated state. This is based on secondary structure propensity and estimation of desolvation penalty to predict β-aggregating regions of a protein sequence as well as mutational effects. In contrast to the models discussed earlier, TANGO takes into account the native state stability by using the FOLD-X force field. Although, it is not possible to calculate absolute rates of aggregation with TANGO, it provides a qualitative comparison between peptides or proteins differing significantly in sequence. Serrano and coworkers (Linding, et al., *J Mol Biol*. 2004, 342, 345-353) have used TANGO to analyze the β-aggregation propensity of a set of non-redundant globular proteins with an upper limit of 40% sequence identity.

A further algorithm, Prediction of Amyloid StrucTure Aggregation (PASTA), was recently introduced by editing a pair-wise energy function for residues facing one another within a β-sheet (Trovato, et al., Protein Engineering, Design & Selection. 2007, 20(10), 521-523; Trovato, et al., PLoS Comput. Biol. 2006, 2, 1608-1618; Trovato et al., *J. Phys.: Condens. Matter.* 2007 19, 285221). Yoon and Welsh (Yoon and Welsh, *Protein Sci.* 2004, 13: 2149-2160) have developed a structure-based approach for detecting β-aggregation propensity of a protein segment conditioned on the number of tertiary contacts. Using a sliding seven-residue window, segments with a strong β-sheet tendency in a tightly packed environment (i.e. with a high number of tertiary contacts) were suggested to be the local mediator of fibril formation.

While the phenomenological models described above were shown to perform well for small peptides and denatured proteins, aggregation propensities might differ for globular proteins such as antibodies where the tertiary structure and the stability of the native state are very important.

Molecular simulation techniques for predicting aggregation prone regions and studying the mechanism of aggregation have mostly employed simpler simulation models (Ma and Nussinov. *Curr. Opin. Chem. Biol.* 2006, 10, 445-452; Cellmer, et al., TRENDS in Biotechnology 2007, 25(6), 254). The least detailed of the simulation models employed was the lattice model, wherein each residue is represented as a bead occupying a single site on a three dimensional lattice. More detailed models, such as the intermediate resolution model followed but suffered from the same inability to accurately represent protein secondary and tertiary structures.

Unlike simpler models, atomistic models include all the atomistic details such as hydrogen bonding and are thus more accurate than the lattice or the intermediate resolution models. Such atomistic models have been used either with an explicit solvent, or with an implicit solvent where the solvent is treated as a continuum. The explicit model is more accurate but also more computationally demanding. Later a molecular dynamics simulation protocol was developed to obtain structural information on ordered β-aggregation of amyloidogenic polypeptides (Cecchini et al., *J Mol Biol*. 2006, 357, 1306-1321.). However, because such a procedure is very computationally demanding, especially for large proteins such as antibodies there does not appear to be full antibody atomistic simulation in the literature. Nevertheless, there have been atomistic simulations of small parts of the antibody, mostly for the Fab fragment (Noon, et al., PNAS. 2002, 99, 6466; Sinha and Smith-Gill, Cell Biochemistry and Biophysics. 2005, 43, 253).

Numerous existing approaches for preventing antibody aggregation employ the use of additives in protein formulations. This is different from the direct approach described herein where antibody itself is modified based on the aggregation prone regions predicted from molecular simulations. Additives commonly used in antibody stabilization are salts of nitrogen-containing bases, such as arginine, guanidine, or imidazole (EP0025275). Other suitable additives for stabilization are polyethers (EPA0018609), glycerin, albumin and dextran sulfate (U.S. Pat. No. 4,808,705), detergents and surfactants such as polysorbatebased surfactants (Publication DA2652636, and Publication GB2175906 (UK Pat. Appl. No. GB8514349)), chaperones such as GroEL (Mendoza, Biotechnol. Tech. 1991, (10) 535-540), citrate buffer (WO9322335) or chelating agents (WO9115509). Although these additives enable proteins to be stabilized to some degree in solution, they suffer from certain disadvantages such as the necessity of additional processing steps for additive removal. Thus, new methods are required to understand the mechanisms involved in protein aggregation and identify the protein regions which mediate this phenomenon. Such methods would be useful in a variety of diagnostic and therapeutic areas, and would allow protein compositions, such as antibody therapeutics, to be directly stabilized without the use of additives.

SUMMARY OF THE INVENTION

The present invention provides methods and computational tools based, at least in part, on computer simulations that identify aggregation prone regions of a protein. Substitutions may then be made in these aggregation prone regions to engineer proteins with enhanced stability and/or a reduced propensity for aggregation.

Furthermore, the present invention provides methods and computational tools based, at least in part, on computer simulations that identify macromolecule binding regions of a protein. Substitutions and deletions may then be made in these macromolecule binding regions to engineer proteins with altered binding affinity for the macromolecule.

In one aspect the invention provides a method for calculating the Spatial-Aggregation-Propensity (SAP) for a particular atom in a protein, comprising (a) identifying one or more atoms in a structural model representing the protein, wherein the one or more atoms are within a defined spatial region centered on or near the particular atom; (b) calculating, for the one or more atoms in the defined spatial region, a ratio of the solvent accessible area (SAA) of the atoms to the SAA of atoms in an identical residue which is fully exposed; (c) multiplying each ratio by the atom hydrophobicity of the one or more atoms; and (d) summing the products of step (c); whereby the sum is the SAP for the particular atom.

In a related embodiment a method for calculating the Spatial-Aggregation-Propensity (SAP) for a particular atom in a protein, comprises (a) identifying one or more amino acid residues in a structural model representing the protein, wherein the one or more amino acid residues have at least one atom within a defined spatial region centered on or near the particular atom; (b) calculating, for the atoms in the defined spatial region, a ratio of the solvent accessible area (SAA) of the atoms to the SAA of atoms in an identical residue which is fully exposed, (c) multiplying each ratio by the hydrophobicity of the one or more amino acid residues as determined by an amino acid hydrophobicity scale; and (d) summing the products of step (c); whereby the sum is the SAP for the particular atom.

It is understood that in particular embodiments the defined spatial region is any 3 dimensional volume or region. In specific embodiments the defined spatial region is selected from the group comprising a sphere, a cube, a cylinder, a pyramid, and an elliptical spheroid. In some embodiments the defined spatial region is a region having a volume equivalent to a sphere with a radius of between 1-30 Å, or more. In some embodiments the radius may be 50 Å or more. In some preferred embodiments the radius of the defined spatial region is 5 Å, or 10 Å.

In a preferred embodiment, the defined spatial region is a sphere having a radius of between 1-30 Å. In some embodiments the sphere is centered on the particular atom, whereas, in other embodiments the defined spatial region or sphere is centered in a chemical bond or centered on a point in space near the atom on which the SAP will be calculated.

In some embodiments the defined spatial region is centered on a point in space within 30 Å from the particular atom or in some preferred embodiments the defined spatial region is centered on a point in space within 20 Å, within 10 Å, within 5 Å, within 2 Å, within 1 Å from the particular atom.

In some embodiments the one or more atoms within the defined spatial region are atoms in a side chain of the one or more amino acids.

In further embodiments one or more atoms within the chosen radius in a structural model may be, or are required to be in a side chain of one or more amino acids. Alternatively, the one or more atoms within the chosen radius in a structural model may be, or are required to be main chain atoms of one or more amino acids.

The Solvent Accessible Area (SAA) which is part of the SAP calculation may, in some embodiments be calculated only on atoms in amino acid side chains, or, in some embodiments only on main chain atoms. The main chain atoms may or may not include the attached hydrogen atoms.

In some particularly preferred embodiments the protein structural model is processed prior to the calculation of the SAP, e.g., by performing a molecular dynamics simulation which optionally includes a solvent. The solvent may be water, another solvent known in the art, or, the solvent may be absent. In some particularly preferred embodiments the protein structural model is processed prior to the calculation of the SAP, e.g., by performing a Monte Carlo simulation.

In another aspect the calculation of the SAP may comprise further performing molecular dynamics simulations and averaging the values of SAP calculated over multiple time steps in the molecular dynamics simulation. For example the SAP for the particular atom may be calculated by conducting a molecular dynamics simulation prior to step (a) above and repeating steps (a)-(d), each time conducting a further molecular dynamics simulation at a plurality of time steps, thereby producing multiple sums as in step (d), and calculating the average of the sums; whereby the calculated average is the SAP for the particular atom. In other examples, a Monte Carlo simulation can be used in place or, or in combination with a molecular dynamics simulation.

In further embodiments the SAP scores may be summed over multiple amino acids, e.g., summing over between 1 and 50 amino acids in an aggregation prone region or surface patch on a protein structural model. In a particularly preferred embodiment, the SAP is summed over 1-20 amino acids, 1-15 amino acids, 1-10 amino acids, 1-5 amino acids, 1-3 amino acids, or the SAP may be summed across 2 adjacent amino acids. In some embodiments, the sum may be taken over adjacent amino acids which may be adjacent sequentially along the protein sequence or spatially in the protein structure.

Wherein the methods call for a molecular dynamics simulation, the simulation may be carried out using a simulation package chosen from the group comprising or consisting of ABINIT, AMBER, Ascalaph, CASTEP, CPMD, CHARMM, DL_POLY, FIREBALL, GROMACS, GROMOS, LAMMPS, MDynaMix, MOLDY, MOSCITO, NAMD, Newton-X, ProtoMol, PWscf, SIESTA, VASP, TINKER, YASARA, ORAC, and XMD. In particularly preferred embodiments, the simulation package is the CHARMM simulation package. In other preferred embodiments the simulation package is the NAMD simulation package.

Wherein the methods call for performing calculations for one or more atoms within a side chain, residue or protein, (e.g., calculating SAA for one or more atoms) it will be appreciate by the skilled artisan that calculations can be for atoms, pairs of atoms, combinations or groups of atoms, portions of atoms, or for each of or all atoms in a spatial region, side chain, residue, protein, etc. When performing calculations featured in the methodologies of the invention, the skilled artisan will also appreciate that calculations (e.g., SAA calculations) can also be made for amino acid residues, side chains, and the like, comprising atoms, groups of atoms, etc.

In further preferred embodiments the structural model is an X-ray crystal structure model of the protein, or portion thereof; or the structural model may be a theoretical protein structure model of the protein, or portion thereof. In related embodiments the theoretical structural model is a homology model of the protein or portion thereof. In other embodiments the theoretical structural model is a an ab initio protein structural model of the protein, or portion thereof.

In another aspect the present invention provides methods to identify aggregation prone regions on a protein. In one embodiment the a method to identify an aggregation prone region on a protein, comprises (a) mapping, onto the structural model the SAP as calculated according any method described herein for atoms in the protein; and (b) identifying a region within in the protein having a plurality of atoms having a SAP>0; wherein the aggregation prone region comprises the amino acids comprising said plurality of atoms. In some embodiments the method may comprise identifying one or more amino acids containing one or more atoms having an SAP greater than a chosen threshold; wherein the SAP is calculated according any method described herein and wherein the aggregation prone region comprises the identified amino acids In another embodiment the method to identify an aggregation prone region on a protein, comprises plotting the SAP values as calculated according any method described herein, further calculating for peaks in the plot the area under the curve (AUC) and identifying one or more protein regions with a positive AUC, wherein the aggregation prone region comprises the identified protein regions.

In another aspect the invention provides methods of making a protein variants which exhibit a reduced propensity for aggregation. In one preferred embodiment a method of making a protein variant which exhibits a reduced propensity for aggregation, comprises replacing or deleting at least one amino acid residue within an aggregation prone region in the protein, wherein the aggregation prone region is identified using SAP scores calculated according any method described herein; and wherein, if the amino acid residue is replaced, it is replaced with an amino acid residue which is more hydrophilic, such that the propensity for aggregation of the variant is reduced. In some particular embodiments at least one residue is replaced and at least one residue is deleted.

In another embodiment a method of making a protein variant which exhibits a reduced propensity for aggregation, comprises (a) generating a plurality of protein variants by replacing, in each variant at least one residue within an aggregation prone region in the protein, wherein the aggregation prone region is identified using SAP scores calculated according any method described herein, wherein one or more different residues, or different combinations of residues are replaced in each variant; wherein the at least one residue is replaced with a residue which is more hydrophilic; and (b) selecting a protein variant prepared as in (a) which exhibits a reduced propensity for aggregation.

In some embodiments the amino acid which is selected for replacement is the most hydrophobic amino acid (as determined by an art-recognized hydrophobicity scale) in an aggregation prone region. In specific embodiments the amino acid selected for replacement is Phe, Leu, Ile, Tyr, Trp, Val, Met, Pro, Cys, Ala, or Gly. In such specific embodiments the more hydrophilic amino acid which is substituted into the protein may be selected from the group consisting of Thr, Ser, Lys, Gln, Asn, His, Glu, Asp, and Arg. Often, the preferred hydrophobicity scale for determining which residues are more or less hydrophilic or hydrophobic than others is the Black and Mould hydrophobicity scale.

In some embodiments at least two amino acid residues within the aggregation prone region are replaced. In related embodiments at least three amino acid residues within the aggregation prone region are replaced. Also, in similar embodiments at least one residue is replaced within more than one aggregation prone regions within the protein.

In preferred embodiments the methods described herein are applied to a protein which is selected from the group consisting of an antibody, a Fab fragment, a Fab' fragment, an Fd fragment, an Fv fragment, an F(ab')$_2$ fragment, and an Fc fragment.

In other preferred embodiments the methods described herein are applied to a protein which is selected from the group consisting of a cytokine, a chemokine, a lipokine, a myokine, a neurotransmitter, a neurotrophin, an interleukin, or an interferon. In some specific embodiments the protein may be a hormone or growth factor, a receptor or receptor domain, or a neurotransmitter or neurotrophin. In some embodiments the protein is a peptidomimetic, a modified protein, a protein comprising unnatural amino acids, or a protein comprising unusual amino acids.

In another aspect the invention also provides methods to calculate the Effective-SAA for an amino acid residue in a protein. A preferred method for calculating the Effective-SAA for an amino acid residue in a protein, comprises (a) calculating for an amino acid a ratio of the solvent accessible area (SAA) of atoms in the amino acid to the SAA of atoms in an identical residue which is fully exposed; (b) multiplying the ratio by the hydrophobicity of the amino acid as determined by an amino acid hydrophobicity scale; whereby the product is the Effective-SAA for the amino acid. In addition, the Effective-SAA for an amino acid residue in a protein may be calculated by a method which further comprises summing the Effective-SAA over 3 amino acids, or in some embodiments 2, 4, 5, or 6 amino acids, which are adjacent in the protein sequence.

In another aspect the invention also includes methods to identify a macromolecule binding region on a protein, comprising (a) mapping, onto a structural model of the protein the SAP as calculated according to any one of the preceding aspects for atoms in the protein; and (b) identifying a region within in the protein having a plurality of atoms having a SAP>0; wherein the macromolecule binding region comprises the amino acids comprising said plurality of atoms.

In another aspect the invention includes methods to identify a macromolecule binding region on a protein, comprising identifying one or more amino acids containing one or more atoms having an SAP greater than a chosen threshold; wherein the SAP is calculated according to the method of any one of the previous aspects and wherein the macromolecule binding region comprises the identified amino acids In another aspect the invention includes methods to identify a macromolecule binding region on a protein, comprising plotting the SAP values as calculated in any one of the preceding aspects, calculating, for peaks in the plot, the area under the curve (AUC) and identifying one or more protein regions with a positive AUC, wherein the macromolecule binding region comprises the identified protein regions.

In another aspect the invention includes methods of making a protein variant which exhibits a reduced binding affinity for a macromolecule, comprising replacing or deleting at least one amino acid residue within a macromolecule binding region for the macromolecule in the protein, wherein the macromolecule binding region is identified using SAP scores calculated according to any one of the previous aspects; and wherein, if the amino acid residue is replaced, it is replaced with an amino acid residue which is more hydrophilic, such that the binding affinity for the macromolecule of the variant is reduced. In certain embodiments at least one residue is replaced and at least one residue is deleted. In another aspect the invention also includes methods of making a protein variant which exhibits an altered binding affinity for a macromolecule, comprising (a) generating a plurality of protein variants by replacing in each variant at least one residue within a macromolecule binding region for the macromolecule in the protein, wherein the macromolecule binding region is identified using SAP scores calculated according to any one of the preceding aspects, wherein one or different residues, or different combinations of residues are replaced in each variant; and (b) selecting a protein variant prepared as in (a) which exhibits an altered binding affinity for the macromolecule. In certain embodiments the at least one amino acid residue within the macromolecule binding region is the most hydrophobic residue in the macromolecule binding region. In certain embodiments the at least one amino acid residue within an aggregation prone region is Phe, Leu, Ile, Tyr, Trp, Val, Met, Pro, Cys, Ala, or Gly. In certain embodiments the amino acid residue which is more hydrophilic is selected from the group consisting of Thr, Ser, Lys, Gln, Asn, His, Glu, Asp, and Arg. In certain embodiments the amino acid residue which is more hydrophilic is an unusual, unnatural, or modified amino acid. In certain embodiments the amino acid residue which is more hydrophilic is determined according to Black and Mould's hydrophobicity scale. In certain embodiments at least two amino acid residues within the macromolecule binding region are replaced. In certain embodiments at least three amino acid residues within the macromolecule binding region are replaced. In certain embodiments at least one residue is replaced within more than one aggregation prone regions within the protein. In certain embodiments the aggregation prone region is identified according to the method of any one of the preceding aspects for identifying an aggregation prone region on a protein. In certain embodiments that may be combined with the preceding embodiments, the macromolecule is another protein, a polynucleotide or a polysaccharide. In certain embodiments that may be combined with the preceding embodiments, the protein is selected from the group consisting of an antibody, a Fab fragment, a Fab' fragment, an Fd fragment, an Fv fragment, an F(ab')$_2$ fragment, and an Fc fragment. In certain embodiments that may be combined with the preceding embodiments, the protein is a cytokine, a chemokine, a lipokine, a myokine, a neurotransmitter, a neurotrophin, an interleukin, or an interferon. In certain embodiments that may be combined with the preceding embodiments, the protein is a hormone or growth factor. In certain embodiments the macromolecule is a hormone receptor or growth factor receptor. In certain embodiments the protein is a receptor or receptor domain. In certain embodiments the macromolecule is a receptor agonist or a receptor antagonist of the receptor or receptor domain. In certain embodiments that may be combined with the preceding embodiments, the protein is a neurotransmitter or neurotrophin. In certain embodiments the macromolecule is a neurotransmitter receptor or neurotrophin receptor.

In another aspect, the invention also includes a method for making a pharmaceutical composition comprising a protein variant which exhibits a altered propensity for interaction with a binding partner, comprising formulating a protein variant obtained according to a process of any of the preceding aspects together with a pharmaceutically acceptable carrier, adjuvant and/or excipient.

DETAILED DESCRIPTION OF THE INVENTION

The present invention addresses the unmet need to more deeply understand the mechanism of protein aggregation, and to identify the protein regions involved in aggregation. The invention provides, at least in part, a simulation technology which can be used, concurrently with the experimental methods described herein, to improve the stability of potentially all therapeutic proteins against aggregation. This technology exhibits enormous scientific and commercial potential considering that antibody based therapies are growing at the highest pace among all classes of human therapeutics. Aggregation is a common problem encountered in most stages of antibody drug development hindering rapid commercialization of potential antibody drug candidates. Thus the prevention of aggregation using the methods described herein could have a significant impact on protein drug development.

In addition, the present invention addresses the unmet need to accurately identify the protein regions involved in binding with other macromolecules which binding is often mediated, at least in part, through large hydrophobic patches that can be readily identified using the methods disclosed herein. The invention provides, at least in part, a simulation technology which can be used, concurrently with the experimental methods described herein, to alter the binding affinity of potentially all protein-molecular interactions that are mediated, at least in part, through large hydrophobic patches. This technology exhibits enormous scientific and commercial potential considering that protein based therapies are growing at the highest pace among all classes of human therapeutics. The ability to alter a protein therapeutic's binding affinity for one or more macromolecules can be used to improve efficacy and reduce or eliminate activities mediated through an unwanted secondary macromolecule binding region.

The present invention provides, inter alia, methods to reduce or prevent aggregation of a protein or alter the binding affinity for a macromolecule. In particular, methods are provided to identify hydrophobic regions on a protein structure which may participate in protein interactions, protein-macromolecule interactions or protein aggregation. The methods provided are based on a new technique disclosed herein as the "Spatial-Aggregation-Propensity" or "SAP." The SAP tool also correctly identifies the regions of the antibody prone to binding with other proteins. In addition to antibodies, this tool could be broadly applied to all proteins for identification of the aggregation prone regions or the regions which bind other proteins or ligands. The methods of the present invention may be applied to any protein for which a three-dimensional structure is available or for which a three-dimensional structure may be created using homology modeling, molecular modeling, or ab initio structure determination. In general, the "SAP" may be calculated in multiple ways, using the equations and methodology described herein, for example, the SAP may be calculated on a protein structural model or may be calculated as an average over multiple time steps of a molecular dynamics simulation of a structural model. Although the specific method of calculation, and the results obtained, may vary as described herein, the underlying principle is based on the fact that SAP is a measure which not only accounts for the hydrophobicity of residues in a protein, but also the protein three-dimensional structure, and the proximity of amino acid residues in the folded protein structure.

By "protein" is meant any sequence of two or more amino acids, (also referred to herein as "amino acid residues" or "residues") joined together by peptide bonds between carboxyl and amino groups of adjacent amino acids, regardless of length, post-translation modification, chemical modification, or function. "Polypeptide," "peptide," and, "protein" are used interchangeably herein. In preferred embodiments, the methods of the present invention are applied to a protein which is of sufficient length to fold into a three-dimensional structure. In some embodiments, the protein is a naturally occurring protein. In some embodiments, the protein is chemically synthesized. In some embodiments the protein is a recombinant protein, for example, a hybrid or chimeric protein. In some embodiments the protein is a complexed protein (e.g., complexed interacting proteins). Proteins can be isolated (e.g., from a natural source or chemical milieu). In some embodiments the protein may be a modified protein or a peptidomimetic. In some embodiments the protein may be a derivatized protein, for example, a chemically conjugated protein (including but not limited to polymer conjugated proteins (e.g., pegylated proteins). As used herein, the term "protein" also is intended to include protein fragments.

Exemplary proteins include antibodies (including but not limited to fragments, variants, and derivatives thereof).

Indeed, it is envisioned that that the methods of the present invention may be applied to any amino acid based molecule for which a structural model is available or may be generated. For example, the methods described herein may be applied to modified proteins, or proteins which incorporate unusual or unnatural amino acids as described herein. In some embodiments, the structures of unusual, unnatural, or modified amino acids may be computationally substituted or inserted into a structural model for application of the methods described herein. Methods of experimentally designing peptide analogs, derivatives and mimetics are known in the art. For example, see Farmer, P. S. in Drug Design (E. J. Ariens, ed.) Academic Press, New York, 1980, vol. 10, pp. 119-143; Ball. J. B. and Alewood, P. F. (1990) *J. Mol. Recognition* 3:55; Morgan, B. A. and Gainor, J. A. (1989) *Ann. Rep. Med. Chem.* 24:243; and Freidinger, R. M. (1989) *Trends Pharmacol. Sci.* 10:270. See also Sawyer, T. K. (1995) "Peptidomimetic Design and Chemical Approaches to Peptide Metabolism" in Taylor, M. D. and Amidon, G. L. (eds.) *Peptide-Based Drug Design: Controlling Transport and Metabolism*, Chapter 17; Smith, A. B. 3rd, et al. (1995) *J. Am. Chem. Soc.* 117:11113-11123; Smith, A. B. 3rd, et al. (1994) *J. Am. Chem. Soc.* 116:9947-9962; and Hirschman, R., et al. (1993) *J. Am. Chem. Soc.* 115:12550-12568.

A great number and variety of peptide, polypeptide, and protein therapeutic agents are known in the art, and are expected to benefit from the methods of the present invention. These therapeutic agents comprise several very broad classes, including hormones, proteins, antigens, immunoglobulins, repressors/activators, enzymes, cytokines, chemokines, myokines, lipokines, growth factors, receptors, receptor domains, neurotransmitters, neurotrophins, interleukins, and interferons among others.

Suitable hormones that can be employed within the scope of the present invention include protein hormones, such as insulin and glucagon which regulate blood sugar. As will be appreciated by one having ordinary skill in the art, the noted hormones are typically employed for treatment of diverse conditions and diseases, including cancer, metabolic diseases, cardiovascular disease, pituitary conditions and menopause.

Initially, it was thought that only some proteins formed fibrils or aggregates. More recent evidence that many more proteins than expected have aggregation prone regions (Fandrich, M., Fletcher, M. A., and Dobson, C. M. (2001) Nature 410, 165-166). Indeed, it is documented that peptides as short as 4 residues can form fibrils (J. Biol. Chem., Vol. 277, Issue 45, 43243-43246, Nov. 8, 2002).

Protein therapeutics represent a growing share of the therapeutic marketplace. For example, insulin and glucagons are important protein therapeutics which regulate blood sugar, are may benefit from the methods described herein. Islet Amyloid Polypeptide (IAPP) is a further hormone secreted by the pancreas which is used in the treatment of diabetes. Another protein of interest is granulocyte colony stimulating factor, or G-CSF, which is a blood growth factor which may be used to increase the production of blood cells. Tissue plasminogen activator is a clot busting used in the treatment of stroke or heart attack. Further, erythropoietin is a hormone produced by the kidney which may be used in the treatment of AIDS, anemia, kidney failure, and other conditions. Finally, calcitonin is a peptide has been found to be effective in the treatment of hypercalcemia, Paget disease, and certain types of osteoporosis.

Further examples of proteins which are expected to benefit from the methods described herein include, without limitation, ACTH, amylin, angiotensin, angiogenin, anti-inflammatory peptides, BNP, endorphins, endothelin, GLIP, Growth Hormone Releasing Factor (GRF), hirudin, insulinotropin, neuropeptide Y, PTH, VIP, growth hormone release hormone (GHRH), octreotide, pituitary hormones (e.g., hGH), ANF, growth factors, bMSH, somatostatin, platelet-derived growth factor releasing factor, human chorionic gonadotropin, hirulog, interferon alpha, interferon beta, interferon gamma, interleukins, granulocyte macrophage colony stimulating factor (GM-CSF), granulocyte colony stimulating factor (G-CSF), menotropins (urofollitropin (FSH) and LH)), streptokinase, urokinase, ANF, ANP, ANP clearance inhibitors, antidiuretic hormone agonists, calcitonin gene related peptide (CGRP), IGF-1, pentigetide, protein C, protein S, thymosin alpha-1, vasopressin antagonists analogs, dominant negative TNF-α, alpha-MSH, VEGF, PYY, and polypeptides, fragments, polypeptide analogs and derivatives derived from the foregoing.

In particularly preferred embodiments, the protein is an antibody or immunoglobulin. The term "antibody" is used in the broadest sense and specifically covers monoclonal antibodies (including full length monoclonal antibodies), polyclonal antibodies, multispecific antibodies (e.g., bispecific antibodies), single chain antibodies, chimeric antibodies, recombinant antibodies, and antibody fragments. A full length antibody is a glycoprotein comprising at least two heavy (H) chains and two light (L) chains inter-connected by disulfide bonds. The Asn-297 residue in $C_{H2}$ is N-glycosylated. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Fc receptors bind at the lower hinge region of $C_{H2}$ and mediate effector functions such as antibody-dependent cell-mediated cytotoxicity (ADCC). Protein A binds at the $C_{H2}$-$C_{H3}$ junction of Fc and is broadly used in the purification of full antibodies. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. Thus, the term "antibody" would encompass the various antibody isotypes or subclasses, e.g., IgA, IgD, IgE, IgG and IgM, or IgG1, IgG2, IgG3, and IgG4. Further included are a Fab fragment, a monovalent fragment consisting of the $V_L$, $V_H$, $C_L$ and $C_H1$ domains; a F(ab')$_2$ fragment, a bivalent fragment comprising two Fab fragments, linked by a disulfide bridge at the hinge region; a Fab' fragment, which is essentially an Fab with part of the hinge region (see, FUNDAMENTAL IMMUNOLOGY (Paul ed., 3rd ed. 1993); a Fd fragment consisting of the $V_H$ and $C_H1$ domains; a Fv fragment consisting of the $V_L$ and $V_H$ domains of a single arm of an antibody, a dAb fragment (Ward et al., (1989) *Nature* 341:544-546), which consists of a $V_H$ domain; an isolated complementarity determining region (CDR); and a nanobody, a heavy chain variable region containing a single variable domain and two constant domains.

As used herein a protein "structural model" is a representation of a protein's three-dimensional secondary, tertiary, and/or quaternary structure. A structural model encompasses X-Ray crystal structures, NMR structures, theoretical protein structures, structures created from homology modeling, Protein Tomography models, and atomistic models built from electron microscopic studies. Typically, a "structural model" will not merely encompass the primary amino acid sequence of a protein, but will provide coordinates for the atoms in a protein in three-dimensional space, thus showing the protein folds and amino acid residue positions. In preferred embodiments, the structural model analyzed is an X-Ray crystal structure, e.g., a structure obtained from the Protein Data Bank (PDB, rcsb.org/pdb/home/home.do) or a homology model built upon a known structure of a similar protein. In preferred embodiments, the structural model will be pre-processed before applying the methods of the present invention. For example, the structural model may be put through a molecular dynamics simulation to allow the protein side chains to reach a more natural conformation, or the structural model may be allowed to interact with solvent, e.g., water, in a molecular dynamics simulation. The pre-processing is not limited to molecular dynamics simulation and can be accomplished using any art-recognized means to determine movement of a protein in solution. An exemplary alternative simulation technique is Monte Carlo simulation. Simulations can be performed using simulation packages or any other acceptable computing means. In certain embodiments, simulations to search, probe or sample protein conformational space can be performed on a structural model to determine movement of the protein.

A "theoretical protein structure" is a three-dimensional protein structural model which is created using computational methods often without any direct experimental measurements of the protein's native structure. A "theoretical protein structure" encompasses structural models created by ab-initio methods and homology modeling. A "homology model" is a three-dimensional protein structural model which is created by homology modeling, which typically involves comparing a protein's primary sequence to the known three dimensional structure of a similar protein. Homology modeling is well known in the art and is described in Kolinski et al. Proteins. 1999; 37(4):592-610; Rost et al., B, Potein Sci. 1996; 5(8):1704-1718, and U.S. Pat. Nos. 7,212,924; 6,256,647; and 6,125,331 which are incorporated herein by reference. In particular, Xiang. (Curr Protein Pept Sci. 2006 June; 7(3):217-27, incorporated herein by reference) provides an excellent description and review of homology modeling techniques which may be used to generate structures useful for the methods of the present invention. Indeed, any homology modeling software known in the art may be used according to the present methods, e.g., MODELLER (Eswar, et al., Comparative Protein Structure Modeling With MODELLER. Current Protocols in Bioinformatics, John Wiley & Sons, Inc., Supplement 15, 5.6.1-5.6.30, 200), SEGMOD/ENCAD (Levitt M. J Mol Biol 1992; 226:507-533), SWISS-MODEL (Schwede T, Kopp J, Guex N, Peitsch M C. Nucleic Acids Research 2003; 31:3381-3385), 3D-JIGSAW (Bates et al., Proteins: Structure, Function and Genetics, Suppl 2001; 5:39-46), NEST (Xiang. *Curr Protein Pept Sci.* 2006 June; 7(3): 217-227), and BUILDER (Koehl and Delarue. Curr Opin Struct Biol 1996; 6(2):222-226.). For antibodies in particular, the structure of antibody variable regions can be obtained accurately using the canonical structures method (Chothia C and Lesk A M, J. Mol. Biol. 1987, 196, 901; Chothia C et al., Nature 1989, 342, 877).

In particular embodiments, homology modeling may be used to assemble full proteins from known structure fragments, such as when an antibody Fab fragment is modeled onto an Fc fragment, or when a Fab fragment is created as a theoretical protein structure and modeled onto a Fc fragment crystal structure. A skilled artisan will understand that various possibilities exist. In one particular embodiment a Fab fragment may be modeled onto various antibody Fc structures of different classes or isotypes.

Ab initio models may also be employed in the methods of the present invention. An "ab initio protein structural model" is a protein structural model which is created directly from the protein primary sequence by simulating the protein folding process using the equations known in physical chemistry (Bonneau and Baker. Annual Review of Biophysics and Biomolecular Structure. 2001, Vol. 30, Pages 173-189; Lesk Proteins 1997; 1:151-166. Suppl; Zemla, et al. Proteins 1997; 1:140-150. Suppl; Ingwall, et al. Biopolymers 1968; 6:331-368; and U.S. Pat. Nos. 6,832,162; 5,878,373; 5,436,850; 6,512,981; 7,158,891; 6,377,893; and U.S. patent application Ser. Nos. 9/788,006; 11/890,863; and Ser. No. 10/113,219, which are all incorporated herein by reference). Typically, experimentally determined structures (e.g., X-Ray crystal structures) and homology models are preferable to ab initio models, since the difficulty in simulating de novo protein folding may, in some cases, lead to imprecise protein structural models.

It is understood that any method known in the art to generate a theoretical protein structure may be useful in accordance with the present invention. In addition to the methods described above, methods such as those described in the meeting, Critical Assessment of Techniques for Protein Structure Prediction (CASP) may be used in the present methodology. Various examples are described in proceedings to CASP, e.g., in the publications related to the 7th Community Wide Experiment on the Critical Assessment of Techniques for Protein Structure Prediction Asilomar Conference Center, Pacific Grove, Calif. Nov. 26-30, 2006 and also in CASP6 proceedings. Proteins: Structure, Function, and Bioinformatics. 2005. 61(57):1-236; CASP5 proceedings. Proteins: Structure, Function, and Genetics. 2003, 53(56):333-595; CASP4 proceedings. Proteins: Structure, Function, and Genetics. 2001, 45(S5):1-199; CASP3 proceedings Proteins: Structure, Function, and Genetics, 1999, 37(53):1-237 (1999)

The present invention also provides a method of making a protein variant which exhibits a reduced propensity for aggregation. As used herein, a "propensity for aggregation" is the tendency of a protein to form clusters or masses. Such clusters or masses may contain two, or more often 3, or more proteins, typically of the same type. Accordingly, a protein which exhibits a "reduced propensity for aggregation" is one which, when modified or treated, forms fewer aggregates or smaller aggregates as compared to the same protein which is unmodified or untreated.

The term "inhibit" is meant to convey a measurable reduction in a phenomenon, often used herein in reference to protein binding interactions or aggregation.

Amino acid residues, clusters of residues, protein regions, peptides, or patches on a protein surface may often be described herein as hydrophilic or hydrophobic. According to the methods of the invention the Spatial-Aggregation-Propensity describes hydrophobicity and is calculated, in part, using an amino acid hydrophobicity scale known in the art. In a preferred embodiment, the amino acid hydrophobicity scale is the scale set forth in Black and Mould, *Anal. Biochem.* 1991, 193, 72-82 (incorporated herein by reference). In general, according to the Black and Mould, amino acid hydrophobicity progresses as follows (beginning with the most hydrophobic residues): Phe>Leu=Ile>Tyr Trp>Val>Met>Pro>Cys>Ala>Gly>Thr>Ser>Lys>Gln> Asn>His>Glu>Asp>Arg. The scaled values for hydrophobicity, as reported by Black and Mould are shown in Table 1 below.

TABLE 1

| | |
|---|---|
| Ala | 0.616 |
| Cys | 0.68 |
| Asp | 0.028 |
| Glu | 0.043 |
| Phe | 1 |
| Gly | 0.501 |
| His | 0.165 |
| Ile | 0.943 |
| Lys | 0.283 |
| Leu | 0.943 |
| Met | 0.738 |
| Asn | 0.236 |
| Pro | 0.711 |
| Gln | 0.251 |
| Arg | 0 |
| Ser | 0.359 |
| Thr | 0.45 |
| Val | 0.825 |
| Trp | 0.878 |
| Tyr | 0.88 |
| Asx | 0.132 |
| Glx | 0.147 |

Accordingly, when an amino acid is selected for replacement by the methods of the invention (e.g., by having a high SAP score or being identified to reside in an aggregation prone region), it will be replaced by another amino acid which is lower on a hydrophobicity scale. For example, if the amino acid Methionine is selected for replacement, it may be replaced with any amino acid which is less hydrophobic, e.g., Pro, Cys, Ala, Gly, etc. In particularly preferred embodiments, a hydrophobic amino acid is replaced with Lys. In further preferred embodiments, a hydrophobic amino acid is replaced with Glu, Gln, Asp, Thr, or Ser. Therefore, when a residue is described as "more hydrophobic," "more hydrophilic," "most hydrophobic," or "most hydrophilic," the determination of hydrophobicity/hydrophilicity is made according to any hydrophobicity scale known in the art, e.g., the preferred scale of Black and Mould.

In practice, any art recognized scale of amino acid hydrophobicity may be employed by the methods of the present invention. Thus, although the scale described in Table 1 may be used during the calculation of Spatial-Aggregation-Propensity, other scales known in the art may be substituted. The recent review by Biswas et al. (J. Chromatogr. A 1000 (2003) 637-655; incorporated herein by reference) describes a variety of hydrophobicity scales which may be used in accordance with the present invention.

In addition to amino acid hydrophobicity, the methods described herein may assign a hydrophobicity to an atom within a protein or protein structural model. In one embodiment the "atom hydrophobicity" is a ratio of the hydrophobicity of the amino acid which comprises the atom and the number of atoms in the amino acid, or more preferably, the number of atoms in the amino acid side chain. In a similar embodiment the "atom hydrophobicity" may be a fraction of the residue hydrophobicity which is proportional to the size, surface area, or volume of the atom in question. For example, if an oxygen atom composes 5% of the volume of an amino acid residue, the atom hydrophobicity of the oxygen atom will be 5% of the hydrophobicity of the amino acid residue. In another embodiment the atom hydrophobicity may be a fraction of the residue hydrophobicity equivalent to or proportional to the fraction of the surface area that the atom contributes to the amino acid residue. In related embodiments, the hydrophobicity weight (i.e., the fraction of residue hydrophobicity) assigned to an atom may reflect the fraction of volume the atom takes up in the residue, the mass weight of the atom in the residue, the contribution of the atom to hydrophobicity, etc. As described above, the amino acid hydrophobicity is determined according to a hydrophobicity scale known in the art.

The term "aggregation prone region" as discussed herein, is a region on a protein structure which has a propensity for binding to other proteins, thus increasing the likelihood for aggregate formation. Aggregation prone regions exhibit hydrophobic character as identified by the SAP scores described herein. In another embodiment, an aggregation prone region is a region which is more hydrophobic than the surrounding regions. In a specific embodiment, the aggregation prone region may be a three-dimensional, defined spatial region, e.g., a sphere of radius R (or, alternatively, all amino acid residues with at least one atom inside radius R), surrounding an atom wherein the hydrophobic character is the SAP score. In further embodiments, the "aggregation prone region" encompasses any cluster or grouping of residues or atoms which exhibit a hydrophobic character as calculated by the SAP score. Alternatively, an "aggregation prone region" may comprise nearby atoms or residues which have an SAP score higher than some threshold, e.g., >−0.5, >0, >0.5, etc, or, in a similar embodiment, it may comprise those atoms or residues having a calculated Area Under the Curve (in a plot of SAP scores as described below) above some threshold, e.g., >−0.5, >0, >0.5, >1, >1.5, >2, >2.5, etc.

In one aspect the methods of the invention employ molecular simulation technology to preprocess protein structural models and/or to identify aggregation prone regions in proteins. For example, a molecular dynamics simulation may be employed to prior to calculating SAP or SAA. In practice, any simulation technique/package that samples conformational space may be used according to the methods described herein. The preferred mode of molecular simulation is a molecular dynamics simulation (MDS). An MDS is a mathematical simulation wherein the atoms in a molecular structure are allowed to move and interact according to the laws of physics, e.g., the chemical bonds within proteins may be allowed to flex, rotate, bend, or vibrate as allowed by the laws of chemistry and physics. Interactions such as electrostatic forces, hydrophobic forces, van der Waals interactions, interactions with solvent and others may also be modeled in MDS simulations. Such simulations allow one of skill in the art to observe the protein structure as it might appear when solvated, or take more accurate measurements on the protein structure by averaging multiple measurements at various points during the simulation. In a preferred embodiment, the molecular simulation is conducted using the CHARMM simulation package (Brooks et al. J. Comput. Chem., 1983, 4, 187). In another preferred embodiment the molecular simulation is conducted using the NAMD package (Phillips et al. Journal of Computational Chemistry. 2005, 26, 1781). One of skill in the art will understand that multiple packages may be used, e.g., the CHARMM package may be employed for setting up or preprocessing a protein structural model, solvating the structure, etc, and the NAMD package may be employed for the simulations which become part of the Spatial-Aggregation-Propensity calculations. Any of the numerous methodologies known in the art to conduct MDS simulations may be used in accordance with the present invention. The following publications, which are incorporated herein by reference, describe multiple methodologies which may be employed: Guvench and MacKerell. Methods Mol Biol. 2008; 443:63-88; Norberg and Nilsson. Q Rev Biophys. 2003 August; 36(3):257-306; U.S. Pat. Nos. 5,424,963; 7,096,167, and U.S. patent application Ser. Nos. 11/520,588; and 10/723,594. In particular, the following software platforms may be employed for molecular dynamics simulations: ABINIT (Gonze et al. Comput. Mat. Science. 2002, 25, 478; Gonze et al. Kristallogr. 2005, 220, 558; abinit.org/); AMBER (Duan et al. Journal of Computational Chemistry. 2003, 24(16):1999-2012; amber.scripps.edu); Ascalaph (agilemolecule.com/Products.html, Jun. 19, 2008); CASTEP (Segall, et al. J. Phys.: Cond. Matt. 2002, 14(11):2717-2743; Clark et al. Zeitschrift für Kristallographie. 2005, 220(5-6) pp. 567-570; castep.org); CPMD (CMPD manual for CMPD version 3.11.0, Mar. 29, 2006; cpmd.org/manual.pdf); CHARMM (Brooks et al. J Comp Chem. 1983, 4:187-217; charmm org); DL_POLY (Todorov & Smith, THE DL POLY 3 USER MANUAL. STFC Daresbury Laboratory. Version 3.09.3, February 2008; cse.scitech.ac.uk/ccg/software/DL_POLY/MANUALS/USRMAN3.09.pdf); FIREBALL (fireball.phys.wvu.edu/LewisGroup/fireballHome.html); GROMACS (Van Der Spoel, et al., J Comput Chem. 2005, 26(16): 1701-18. Hess, et al, J Chem Theory Comput. 2008, 4(2): 435; gromacs.org); GROMOS (Schuler, Daura, van Gunsteren. Journal of Computational Chemistry. 2001, 22(11):1205-1218; igc.ethz.ch/GROMOS/index); LAMMPS (Plimpton, J Comp Phys. 1995, 117, 1-19; lammps.sandia.gov); MDynaMix (Lyubartsev and Laaksonen. Computer Physics Communications. 2000, 128, 565-589; fos.su.se/~sasha/mdynamix/); MOLDY (Moldy: a portable molecular dynamics simulation program for serial and parallel computers, Computer Physics Communications. 2000, 126(3):309-328; earth.ox.ac.uk/~keithr/moldy.html); MOSCITO (Dietmar Paschek and Alfons Geiger. User's Guide and Manual, MOSCITO 4, Performing Molecular Dynamics Simulations, Apr. 7, 2003, ganter.chemie.uni-dortmund.de/MOSCITO/manual4.pdf); NAMD (Kumar, et al. IBM Journal of Research and Development. 2007, Volume 52, No. 1/2; Phillips et al., Proceedings of SC 2002; charm.cs.uiuc.edu/research/moldyn/); Newton-X (M. Barbatti, G. Granucci, M. Ruckenbauer, M. Persico, H. Lischka, Newton-X: a package for Newtonian dynamics close to the crossing seam, version 0.15b, 2007; univie.ac.at/newtonx; Barbatti, et al., J. Photochem. Photobio. A 190, 228 (2007)); ProtoMol (Matthey, et al. ACM Trans. Math. Softw., 2004, 30(3):237-265; protomol.sourceforge.net/); PWscf (User's Guide for Quantum-ESPRESSO version 3.2, pwscf.org/guide/3.2.3/users-guide-3.2.3.pdf); SIESTA (Soler, et al. Journal of Physics: Condensed Matter. 2002, 14: 2745-2779; uam.es/departamentos/ciencias/fismateriac/siesta/); VASP (Georg Kresse and Jurgen Furthmüller, VASP the GUIDE, Institut für Materialphysik, Universitat Wien, Sensengasse 8, A-1130 Austria, Vienna, Mar. 1, 2007; cms.mpi.univie.ac.at/vasp/); TINKER (Ren and Ponder. J. Phys. Chem. B. 2003, 107, 5933-5947; dasher.wustl.edu/tinker/); YASARA (Krieger E, Koraimann G, Vriend G. Proteins. 2002 47(3):393-402); ORAC (Procacci, et al., Phys. Chem. 1996, 100 10464-10469; chim.unifi.it/orac/); XMD (XMD online manual, XMD—Molecular Dynamics Program Jon Rifkin, v2.5.30 20 Jan. 2002)

As used herein, the terms "amino acid" and "amino acid residue" and "residue" may, in some embodiments, be used synonymously to refer to an amino acid as it exists in an isolated state, e.g., in solution have unbound amino and carboxy terminal groups, or as it exists in a protein, e.g., an amino acid residue covalently linked to at least one other amino acid via a peptide bond. One of skill in the art will understand the intended protein chemistry.

As used herein, an "unnatural amino acid" is an amino acid which is not known to occur in nature. The term "unnatural amino acid" encompasses amino acid analogs. It may further encompass a derivative of a natural amino acid comprising a substitution or addition selected from the group comprising an alkyl group, an aryl group, an acyl group, an azido group, a cyano group, a halo group, a hydrazine group, a hydrazide group, a hydroxyl group, an alkenyl group, an alkynl group, an ether group, a thiol group, a sulfonyl group, a seleno group, an ester group, a thioacid group, a borate group, a boronate group, a phospho group, a phosphono group, a phosphine group, a heterocyclic group, an enone group, an imine group, an aldehyde group, a hydroxylamino group, a keto group, a sugar group, .alpha.-hydroxy group, a cyclopropyl group, a cyclobutyl group, a cyclopentyl group, a 2-nitrobenzyl group, a 3,5-dimethoxy-2-nitrobenzyl group, a 3,5-dimethoxy-2-nitroveratrole carbamate group, a nitrobenzyl group, a 3,5-dimethoxy-2-nitrobenzyl group, and an amino group.

For example, unnatural amino acid may be, without limitation, any of the following amino acids: hydroxy methionine, norvaline, O-methylserine, crotylglycine, hydroxy leucine, allo-isoleucine, norleucine, α-aminobutyric acid, t-butylalanine, hydroxy glycine, hydroxy serine, F-alanine, hydroxy tyrosine, homotyrosine, 2-F-tyrosine, 3-F-tyrosine, 4-methyl-phenylalanine, 4-methoxy-phenylalanine, 3-hydroxy-phenylalanine, 4-NH$_2$-phenylalanine, 3-methoxy-phenylalanine, 2-F-phenylalanine, 3-F-phenylalanine, 4-F-phenylalanine, 2-Br-phenylalanine, 3-Br-phenylalanine, 4-Br-phenylalanine, 2-Cl-phenylalanine, 3-Cl-phenylalanine, 4-Cl-phenylalanine, 4-CN-phenylalanine, 2,3-F$_2$-phenylalanine, 2,4-F$_2$-phenylalanine, 2,5-F$_2$-phenylalanine, 2,6-F$_2$-phenylalanine, 3,4-F$_2$-phenylalanine, 3,5-F$_2$-phenylalanine, 2,3-Br$_2$-phenylalanine, 2,4-Br$_2$-phenylalanine, 2,5-Br$_2$-phenylalanine, 2,6-Br$_2$-phenylalanine, 3,4-Br$_2$-phenylalanine, 3,5-Br$_2$-phenylalanine, 2,3-Cl$_2$-phenylalanine, 2,4-Cl$_2$-phenylalanine, 2,5-Cl$_2$-phenylalanine, 2,6-Cl$_2$-phenylalanine, 3,4-Cl$_2$-phenylalanine, 2,3,4-F$_3$-phenylalanine, 2,3,5-F$_3$-phenylalanine, 2,3,6-F$_3$-phenylalanine, 2,4,6-F$_3$-phenylalanine, 3,4,5-F3-phenylalanine, 2,3,4-Br$_3$-phenylalanine, 2,3,5-Br$_3$-phenylalanine, 2,3,6-Br$_3$-phenylalanine, 2,4,6-Br$_3$-phenylalanine, 3,4,5-Br$_3$-phenylalanine, 2,3,4-Cl$_3$-phenylalanine, 2,3,5-Cl$_3$-phenylalanine, 2,3,6-Cl$_3$-phenylalanine, 2,4,6-Cl$_3$-phenylalanine, 3,4,5-Cl$_3$-phenylalanine, 2,3,4,5-F$_4$-phenylalanine, 2,3,4,5-Br$_4$-phenylalanine, 2,3,4,5-Cl$_4$-phenylalanine, 2,3,4,5,6-F$_5$-phenylalanine, 2,3,4,5,6-Br$_5$-phenylalanine, 2,3,4,5,6-Cl$_5$-phenylalanine, cyclohexylalanine, hexahydrotyrosine, cyclohexanol-alanine, hydroxyl alanine, hydroxy phenylalanine, hydroxy valine, hydroxy isoleucine, hydroxyl glutamine, thienylalanine, pyrrole alanine, N$_T$-methyl-histidine, 2-amino-5-oxohexanoic acid, norvaline, norleucine, 3,5-F$_2$-phenalanine, cyclohexyalanine, 4-Cl-phenylalanine, p-azido-phenylalanine, o-azido-phenylalanine, O-4-allyl-L-tyrosine, 2-amino-4-pentanoic acid, and 2-amino-5-oxohexanoic acid. It is expected that, at least for the unnatural amino acids listed above and for those employed by the Ambrx ReCODE™ technology (ambrx.com/wt/page/technology), the unnatural amino acids will follow hydrophobicity scales similar to that of the common 20 amino acids, e.g., as described in Black and Mould. Alternatively, the hydrophobicity of any unnatural or unusual amino acid may be determined by various techniques which are well known in the art, such as those reviewed and referenced in Biswas et al. (*J. Chromatogr. A* 1000 (2003) 637-655).

The term "amino acid analog" refers to an amino acid wherein the C-terminal carboxy group, the N-terminal amino group or side-chain functional group has been chemically modified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "unusual amino acid" refers to those natural amino acids which are rare or otherwise not among the most common amino acids wherein the common amino acids are selenocysteine, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

Further non-limiting examples of the modified, unusual (i.e., rare), unnatural, or analog amino acids which may be substituted into a protein according to the methods of the invention are: O-methyl-L-tyrosine, L-3-(2-naphthyl)-alanine, 3-methyl-L-phenylalanine, fluorinated phenylalanine, p-benzoyl-L-phenylalanine, p-iodo-L-phenylalanine, p-bromo-L-phenylalanine, p-amino-L-phenylalanine, 3,4-dihydroxy-L-phenylalanine, isopropyl-L-phenylalanine, p-azido-L-phenylalanine, p-acetyl-L-phenylalanine, m-acetyl-L-phenylalanine, 4-(2-oxo-propoxy)-L-phenylalanine, and the amino acids (and methods of incorporating the same) which are described in U.S. Pat. Nos. 7,083,970; 7,045,337; U.S. patent application Ser. Nos. 10/126,931; 11/002,387; 11/254,170; 11/009,635; 11/670,354; 11/284, 259; 10/563,686; 11/326,970; 10/563,656; 10/563,655; 11/715,672; 11/671,036; 11/255,601; 11/580,223; 11/137, 850; 11/233,508; 10/575,991; 11/232,425; Wipo Publications WO/2007/094916; WO/2007/130453; and the publications Liao J. Biotechnol Frog. 2007 January-February; 23(1):28-31; Rajesh, and Iqbal. Curr Pharm Biotechnol. 2006 August; 7(4):247-59. Cardillo et al. Mini Rev Med Chem. 2006 March; 6(3):293-304; Wang et al. Annu Rev Biophys Biomol Struct. 2006; 35:225-49; Chakraborty et al., Glycoconj J. 2005 March; 22(3):83-93 which are all incorporated herein by reference. Further examples of unnatural amino acids can be found, for example, in the following U.S. Patent Publications, the contents of which are hereby incorporated by reference: 2003-0082575, 2005-0250183, 2003-0108885, 2005-0208536, and 2005-0009049.

I. Spatial-Aggregation-Propensity

The invention herein relates to methods for identifying aggregation prone regions on a protein surface, for preventing or reducing aggregation of a protein, and for identifying a macromolecule binding region on a protein. The methods herein represent an advancement in the ability of computational methods to identify protein regions which may be modified to reduce the propensity of a protein from aggregating or to reduce the binding affinity of a protein for a macromolecule. In particular, the methods are based, at least in part, on the calculation of the SAA (Solvent Accessible Area), which is known in the art for characterizing the surface of a protein. SAA gives the surface area of each amino acid or protein structure that is in contact with the solvent. SAA may be typically calculated by computing the locus of the center of a probe sphere as it rolls over the protein surface, i.e., the surface of a protein structural model. The probe sphere has the same radius as that of a water molecule, R=1.4 Å. Alternative methods of calculating SAA, described below, are known in the art and are compatible with the methods described herein. Although SAA is quite useful to characterize the protein surface, it was not found to be adequate to characterize the hydrophobic patches on the protein surface that are potentially aggregation prone because of the following shortcomings, 1. SAA doesn't distinguish between hydrophobic and hydrophilic regions
2. SAA is not directly proportional to a residue's hydrophobicity (for example, MET has more surface area than LEU but is less hydrophobic)
3. SAA doesn't indicate whether several hydrophobic residues are close-by and thus could enhance the hydrophobicity of a certain region. These residues could be close-by either in primary sequence or in the tertiary structure even though they are far in primary sequence. Either way, they could enhance the hydrophobicity of a certain patch on the antibody surface.

One measure which is described herein, the Effective-SAA, is generated by calculating the hydrophobicity of the fraction of the amino acid which is exposed according to the formula below:

$$\text{Effective-}SAA = \frac{SAA}{SAA_{fully\ exposed}} \times \text{Residue hydrophobicity}$$

A further embodiment of the Effective-SAA further comprises summing the Effective-SAA over at least to, at least three, at least four, at least five or at least six, (e.g., two, three, four, five, six, etc.) amino acid residues which are adjacent in the primary protein sequence. Although the Effective-SAA represents an improvement over the basic SAA, it nevertheless lacks the ability to fully account for the structure of the folded protein and for the fact that amino acids which are not adjacent in the protein sequence may be in proximity to one another in the folded secondary, tertiary, or quaternary structure of a protein. Such protein folds may form aggregation prone regions which do not appear in the primary structure alone, or which may only be detected by more robustly analyzing the folded protein structure.

The present invention provides a new, more advanced measure, called the Spatial-Aggregation-Propensity, which will highlight the effective hydrophobicity of a certain patch or region on the protein surface. The Spatial-Aggregation-Propensity is calculated for defined spatial regions on or near the atoms of a protein structural model.

In this context, a "defined spatial region" is a three-dimensional space or volume chosen to capture a local physical structure and/or chemical environment on or near the protein structure. In a particularly preferred embodiment the Spatial-Aggregation-Propensity is calculated for spherical regions with radius R centered on atoms in a protein (e.g., atoms in a protein structural model). The Spatial-Aggregation-Propensity may also be calculated for spherical regions with radius R centered on chemical bonds, or positioned in space near the structural model. Accordingly, in another preferred embodiment the SAP may be calculated for a defined spatial region centered near an atom, e.g., centered on a point in space which is between 1-10 Å, more preferably 1-5 Å, more preferably 1-2 Å from the center of a particular atom or chemical bond.

In preferred embodiments, the chosen radius R is between 1 Å and 50 Å, more preferably between 1 Å and 50 Å. In particular embodiments the chosen radius is at least 1 Å, at least 3 Å, at least 4 Å, at least 5 Å, at least 6 Å, at least 7

Å, at least 8 Å, at least 9 Å, at least 10 Å, at least 11 Å, at least 12 Å, at least 15 Å, at least 20 Å, at least 25 Å, or at least 30 Å. In particularly preferred embodiments, the chosen radius is between 5 Å and 15 Å, more preferably between 5 Å and 12 Å, more preferably between 5 Å and 10 Å. In specific embodiments the chosen radius is 5 Å or 10 Å.

In further embodiments, the region for which the Spatial-Aggregation-Propensity is calculated is not spherical. The possible shape of the region may further comprise a cube, a cylinder, a cone, elliptical spheroid, a pyramid, a hemisphere, or any other shape which may be used to enclose a portion of space. In such embodiments, the size of the region may be chosen using measures other than radius, e.g., the distance from the center of the shape to a face or vertex.

In a preferred embodiment, the SAP may be used to select residues in a protein which may be substituted, thus increasing the protein's stability. In previous studies two main approaches to stabilize a protein in vitro have been to (1) engineer the protein sequence itself and (2) include additives in the liquid formulation. Both approaches have been investigated and significant results have been obtained. The first approach has relied on screening extensive libraries of random variants in silico or experimentally. In the second approach, high-throughput screening for stabilizing additives, as well as rational design of additives permits identification of optimal formulations for a therapeutic protein.

The present invention is expected to streamline the process of stability enhancement by identifying existing hotspots for aggregation computationally, and analyzing variants with substitutions at those sites experimentally.

Thus, in general terms, a method for calculating the Spatial-Aggregation-Propensity for a particular atom in a protein comprises (a) identifying one or more atoms in a structural model representing the protein, wherein the one or more atoms are within a defined spatial region centered on or near the particular atom; (b) calculating, for each of the one or more atoms in the defined spatial region, a ratio of the solvent accessible area (SAA) of the atoms to the SAA of atoms in an identical residue which is fully exposed; (c) multiplying each ratio by the atom hydrophobicity of the one or more atoms; and (d) summing the products of step (c); whereby the sum is the SAP for the particular atom.

In a related embodiment, the SAP may be calculated according to a different method comprising (a) identifying one or more amino acid residues in a structural model representing the protein, wherein the one or more amino acid residues have at least one atom within a defined spatial region centered on or near the particular atom; (b) calculating, for each of the identified one or more amino acid residues, a ratio of the solvent accessible area (SAA) of atoms in the amino acid to the SAA of atoms in an identical residue which is fully exposed; (c) multiplying each ratio by the hydrophobicity of the one or more amino acid residues as determined by an amino acid hydrophobicity scale; and (d) summing the products of step (c); whereby the sum is the SAP for the particular atom. In preferred embodiments, the structural model is processed prior to step (a) by allowing the structural model to interact with solvent in a molecular dynamics simulation. When an amino acid is identified as having at least one atom within the defined spatial region, the at least one atom may be required to be exclusively an atom in an amino acid side chain. Alternatively it may be an atom required to be a main chain atom.

In other embodiments, this method may further comprise optionally conducting a molecular dynamics simulation prior to step (a) and repeating steps (a)-(d), each time conducting a further molecular dynamics simulation at a plurality of time steps, thereby producing multiple sums as in step (d), and calculating the average of the sums; whereby the calculated average is the SAP for the particular atom.

In other preferred embodiments, the SAP may be used to select residues in a protein which may be substituted, thus reducing the protein's binding affinity for a macromolecule.

One of skill in the art will appreciate that an embodiment of the present invention which employs the average of values calculated over a molecular dynamics simulation will be more computationally intensive. Such an embodiment will also, in some cases, provide a more precise or highly resolved map of the Spatial-Aggregation-Propensity. However, experiments discussed herein have shown that the method is still highly accurate when the molecular dynamics averaging is not employed. In one preferred embodiment, Spatial-Aggregation-Propensity values may be calculated for all protein structures in a database, e.g., the Protein Data Bank (PDB, thereby swiftly identifying hydrophobic residues and patches on all known protein structures. This method allows rapid screening of large sets of proteins to identify potential aggregation prone regions and/or protein interaction sites.

In a preferred application, the Spatial-Aggregation-Propensity is described by the following formula:

$$(\text{Spatial-aggregation-propensity}(SAP))_{atom\ i} = \sum_{\substack{Simulation \\ Average}} \left\{ \sum_{\substack{atoms\ within \\ R\ from\ atom\ i}} \left( \frac{SAA \text{ of side chain atoms within radius } R}{SAA \text{ of side chain atoms of fully exposed residue}} \times \text{Atom hydrophobicity} \right) \right\}$$

wherein
1) SAA of side chain atoms within radius R is computed at each simulation snapshot. SAA is preferably calculated in the simulation model by computing the locus of the center of a probe sphere as it rolls over the protein surface. The probe sphere has the same radius as that of a water molecule, R=1.4 A. One of skill in the art will appreciate that other methods of computing the SAA would be compatible with the methods described here to calculate SAP. For example, the SAA may be calculated on only amino acid side chain atoms. The SAA may also be calculated on only amino acid main chain atoms (i.e., those atoms of the peptide backbone and associated hydrogens). Alternatively, the SAA may be calculated on only amino acid main chain atoms with the exclusion of associated hydrogens;
2) SAA of side chain of fully exposed residue (say for amino acid 'X') is obtained, in a preferred embodiment, by calculating the SAA of side chains of the middle residue in the fully extended conformation of tripeptide 'Ala-X-Ala'; and
3) Atom Hydrophobicity is obtained as described above using the hydrophobicity scale of Black and Mould (Black and Mould, Anal. Biochem. 1991, 193, 72-82).

A residue which is "fully exposed" is a residue, X, in the fully extended conformation of the tripeptide Ala-X-Ala. One of skill in the art will appreciate that this arrangement is designed such that a calculation of SAA on such a residue, X, will yield the maximum solvent accessible area available. Accordingly, it is contemplated that other residues besides alanine may be used in the calculation without wholly disrupting or altering the results.

As described above, the methods of the present invention may be applied to any protein structural model. Accordingly the SAP based on just the X-ray structure can be set forth as:

$$(\text{Spatial-aggregation-propensity}(SAP))_{\text{atom } i}^{X\text{-ray}} = \sum_{\substack{\text{Simulation} \\ \text{Average}}} \left\{ \sum_{\substack{\text{atoms within} \\ R \text{ from atom } i}} \left( \frac{\text{SAA of side chain atoms within radius } R}{\text{SAA of side chain atoms of fully exposed residue}} \times \text{Atom hydrophobicity} \right) \right\}$$

Similarly, if the X-ray structure is not available, the same Spatial-Aggregation-Propensity parameter can be applied to the structure generated through homology modeling, and the SAP parameter may thus be set forth as:

$$(\text{Spatial-aggregation-propensity}(SAP))_{\text{atom } i}^{\text{Homology structure}} = \sum_{\substack{\text{Simulation} \\ \text{Average}}} \left\{ \sum_{\substack{\text{atoms within} \\ R \text{ from atom } i}} \left( \frac{\text{SAA of side chain atoms within radius } R}{\text{SAA of side chain atoms of fully exposed residue}} \times \text{Atom hydrophobicity} \right) \right\}$$

In preferred embodiments the Spatial-Aggregation-Propensity is calculated for all atoms in a protein structural model. In some embodiments, the atomistic Spatial-Aggregation-Propensity values may be averaged over each individual protein residue, or over small groups of residues.

II. Uses of the Invention

In one aspect, the present invention may be used as described above to identify hydrophobic amino acid residues, regions or patches in a protein. Without wanting to be held to specific threshold values, atoms or amino acid residues having a Spatial-Aggregation-Propensity $>0$ are considered to be hydrophobic, or to be in an aggregation prone region. Depending on the type of protein, the particular structure, and the solvent in which it exists, it may be desirable to identify atoms or residues using a cutoff which is slightly below zero, e.g., by choosing atoms or residues which have a Spatial-Aggregation-Propensity of greater than $-0.1$, $-0.15$, $-0.2$, etc. Alternatively, it may be desirable to employ a more stringent cutoff, e.g., 0, 0.05, 0.1, 0.15, 0.2, etc., in order to choose the strongest hydrophobic atoms, residues, or patches. In another embodiment, it may be advantageous simply to select atoms or residues having Spatial-Aggregation-Propensity which is larger than atoms or residues which are nearby either sequentially (i.e., along the protein sequence) or, in a preferred embodiment, spatially (i.e., in the three-dimensional structure). One preferred method for selecting atoms or residues in a hydrophobic patch is to map the calculated Spatial-Aggregation-Propensity values, e.g., using a color coding or numerical coding, onto the protein structural model from which they were derived, thus visualizing differences in the Spatial-Aggregation-Propensity across the protein surface and hence allowing easy selection of hydrophobic patches or residues. In a particularly preferred embodiment, the calculations for Spatial-Aggregation-Propensity are carried out separately using two values chosen for the radius, one of higher resolution, e.g., 5 Å, and one of lower resolution, e.g., 10 Å. In such an embodiment larger or broader hydrophobic patches may be seen on the protein structure with the lower resolution map. Once hydrophobic patches of interest are selected on the low resolution map, those patches may be viewed in greater detail in the higher resolution map which may, in some embodiments, allow one of skill in the art to more easily or more accurately choose residues to mutate or modify. For example, when viewing a hydrophobic patch in the higher resolution map, it may be desirable to select for mutation the residue which has the highest SAP score or is the most hydrophobic (e.g., the most hydrophobic residue in the patch according to the scale of Black and Mould, *Anal. Biochem.* 1991, 193, 72-82).

In a specific embodiment a method to identify an aggregation prone region on a protein comprises (a) mapping, onto the structural model the SAP as calculated according to any of the methods described herein for atoms in the protein; and (b) identifying a region within in the protein having a plurality of atoms having a SAP>0; wherein the aggregation prone region comprises the amino acids comprising said plurality of atoms. In such an embodiment the SAP may be calculated for all the atoms in a protein or a portion of the atoms. It is contemplated that one may only calculate the SAP for particular residues or groups of residues which are of interest.

In a similar embodiment, it may be informative to plot the SAP scores of the atoms (or the SAP score as averaged over amino acid residues). Such a plot showing the SAP score along the atoms or residues of a protein allows the easy identification of peaks, which may indicate candidates for replacement. In a particularly preferred embodiment the SAP scores along the atoms or residues in the protein are plotted in a graph and the Area Under the Curve (AUC) is calculated for peaks in the graph. In such an embodiment, peaks with a larger AUC represent larger or more hydrophobic aggregation prone regions. In particular embodiments it will be desirable to select for replacement one or more residues which are identified as existing in a peak, or, more preferably, in a peak with a large AUC.

In particular embodiments the present invention may be used to make a protein variant which exhibits a reduced propensity for aggregation by replacing at least one amino acid residue within an aggregation prone region in the protein identified by any of the methods described herein with an amino acid residue which is more hydrophilic then the residue which is being replaced, such that the propensity for aggregation of the variant is reduced. As used herein, when amino acid residues are referred to as "more" or "less" hydrophilic or hydrophobic, it will be appreciated by the skilled artisan that this signifies more or less hydrophobic as compared to another amino acid according to a measure of hydrophobicity (hydrophilicity) known in the art, e.g., the hydrophobicity scale of Black and Mould.

In a similar embodiment the present invention may be used to make a protein variant which exhibits a reduced propensity for aggregation by generating a plurality of protein variants by replacing, in each variant at least one residue within an aggregation prone region in the protein, wherein the aggregation prone region is identified using SAP scores calculated according any method described herein, wherein one or different residues, or different combinations of residues are replaced in each variant, and wherein the at least one residue is replaced with a residue which is more hydrophilic; and (b) selecting a protein variant prepared as in (a) which exhibits a reduced propensity for aggregation.

In addition, an amino acid residue in an aggregation prone region may be deleted rather than replaced. In some proteins where multiple amino acid residues are selected for replacement, some residues may be replaced while others are deleted.

In further embodiments multiple aggregation prone regions or residues may be identified in an initial protein by the methods described above (e.g., by using a Spatial-Aggregation-Propensity cutoff above which residues are selected). Subsequently, a plurality of protein variants may be generated by replacing in said initial protein one or more selected amino acid residues (or one or more residues falling in selected patch) with amino acid residues which are more hydrophilic, such that a plurality of protein variants are created representing a variety of different amino acid substitutions. This population may then be screened to select one or more protein variants which have a reduced propensity for aggregation. One of skill in the art will appreciate that multiple aggregation prone regions may be identified, and that one or more substitutions and/or deletions may be made in one or more aggregation prone regions. The relative hydrophobicity of the amino acids may be determined by the hydrophobicity scale of Black and Mould as described above. In specific embodiments, an amino acid to be replaced is selected from the group comprising or consisting of Phe, Leu, Ile, Tyr, Trp, Val, Met, Pro, Cys, Ala, or Gly. In related embodiments, the more hydrophilic amino acid which will be substituted into the protein will be chosen from the group comprising or consisting of Thr, Ser, Lys, Gln, Asn, His, Glu, Asp, and Arg.

Protein variants may be made by any method known in the art including site directed mutagenesis and other recombinant DNA technology, e.g., see U.S. Pat. Nos. 5,284,760; 5,556,747; 5,789,166; 6,878,531, 5,932,419; and, 6391548 which are incorporated herein by reference.

In particular embodiments the present invention may be used to make a protein variant which exhibits a reduced propensity for aggregation by replacing at least one amino acid residue within an aggregation prone region in the protein identified by any of the methods described herein with a natural amino acid residue, a modified amino acid residue, an unusual amino acid residue, an unnatural amino acid residue, or an amino acid analog or derivative which is more hydrophilic then the residue which is being replaced, such that the propensity for aggregation of the variant is reduced.

The synthesis of unnatural amino acids is known to those of skill in the art, and is further described, e.g., in U.S. Patent Publication No. 2003-0082575. In general, any method known in the art to synthesize or incorporate unnatural, modified, or unusual amino acids into proteins may be employed including, but not limited to those methods described or referenced in the publications Liao J. Biotechnol Frog. 2007 January-February; 23(1):28-31; Rajesh, and Iqbal. Curr Pharm Biotechnol. 2006 August; 7(4):247-59; Cardillo et al. Mini Rev Med Chem. 2006 March; 6(3):293-304; Wang et al. Annu Rev Biophys Biomol Struct. 2006; 35:225-49; Chakraborty et al., and Glycoconj J. 2005 March; 22(3):83-93 which are all incorporated herein by reference. As a further example, the Ambrx ReCODE™ technology may be employed to develop and incorporate unnatural amino acids, or unusual amino acids into proteins as indicated by the methods described herein.

Protein variants according to the invention can exhibit enhanced or improved stability as determined, for example, by accelerated stability studies. Exemplary accelerated stability studies include, but are not limited to, studies featuring increased storage temperatures. A decrease in the formation of aggregates observed for a protein variant as compared to the wild type or initial protein indicates an increased stability. Stability of protein variants may also be tested by measuring the change in the melting temperature transition of a variant as compared to the wild type or initial protein. In such an embodiment, increased stability would be evident as an increase in the melting temperature transition in the variant. Additional methods for measuring protein aggregation are described in U.S. patent application Ser. No. 10/176, 809 which is incorporated herein by reference.

In another aspect of the invention the calculated Spatial-Aggregation-Propensity may be used to identify protein-protein interaction sites on the surface of a protein structure. It is known in the art that protein interaction sites often contain hydrophobic residues or hydrophobic patches. It is expected that the methods described herein will be useful in locating binding sites by identifying hydrophobic patches. Such hydrophobic patches will then be candidates for protein-protein or protein-ligand recognition sites.

In another aspect the invention also includes methods to identify a macromolecule binding region on a protein, comprising (a) mapping, onto a structural model of the protein the SAP as calculated according to any one of the preceding aspects for atoms in the protein; and (b) identifying a region within in the protein having a plurality of atoms having a SAP>0; wherein the macromolecule binding region comprises the amino acids comprising said plurality of atoms.

In another aspect the invention includes methods to identify a macromolecule binding region on a protein, comprising identifying one or more amino acids containing one or more atoms having an SAP greater than a chosen threshold; wherein the SAP is calculated according to the method of any one of the previous aspects and wherein the macromolecule binding region comprises the identified amino acids In another aspect the invention includes methods to identify a macromolecule binding region on a protein, comprising plotting the SAP values as calculated in any one of the preceding aspects, calculating, for peaks in the plot, the area under the curve (AUC) and identifying one or more protein regions with a positive AUC, wherein the macromolecule binding region comprises the identified protein regions.

In another aspect the invention may be used to make a protein variant which exhibits a reduced binding affinity for a macromolecule, comprising replacing or deleting at least one amino acid residue within a macromolecule binding region for the macromolecule in the protein, wherein the macromolecule binding region is identified using SAP scores calculated according to any one of the previous aspects; and wherein, if the amino acid residue is replaced, it is replaced with an amino acid residue which is more hydrophilic, such that the binding affinity for the macromolecule of the variant is reduced. In certain embodiments at least one residue is replaced and at least one residue is deleted. In another aspect the invention also includes methods of making a protein variant which exhibits an altered binding affinity for a macromolecule, comprising (a) generating a plurality of protein variants by replacing in each variant at least one residue within a macromolecule binding region for the macromolecule in the protein, wherein the macromolecule binding region is identified using SAP scores calculated according to any one of the preceding aspects, wherein one or different residues, or different combinations of residues are replaced in each variant; and (b) selecting a protein variant prepared as in (a) which exhibits an altered binding affinity for the macromolecule. In certain embodiments the at least one amino acid residue within the macromolecule binding region is the most hydrophobic residue in the macromolecule binding region. In certain embodiments the at least one amino acid residue within an aggregation prone region is Phe, Leu, Ile, Tyr, Trp, Val, Met, Pro, Cys, Ala, or Gly. In certain embodiments the amino acid residue which is more hydrophilic is selected from the group consisting of Thr, Ser, Lys, Gln, Asn, His, Glu, Asp, and Arg. In certain embodiments the amino acid residue which is more hydrophilic is an unusual, unnatural, or modified amino acid. In certain embodiments the amino acid residue which is more hydrophilic is determined according to Black and Mould's hydrophobicity scale. In certain embodiments at least two amino acid residues within the macromolecule binding region are replaced. In certain embodiments at least three amino acid residues within the macromolecule binding region are replaced. In certain embodiments at least one residue is replaced within more than one aggregation prone regions within the protein. In certain embodiments the aggregation prone region is identified according to the method of any one of the preceding aspects for identifying an aggregation prone region on a protein. In certain embodiments that may be combined with the preceding embodiments, the macromolecule is another protein, a polynucleotide or a polysaccharide. In certain embodiments that may be combined with the preceding embodiments, the protein is selected from the group consisting of an antibody, a Fab fragment, a Fab' fragment, an Fd fragment, an Fv fragment, an $F(ab')_2$ fragment, and an Fc fragment. In certain embodiments that may be combined with the preceding embodiments, the protein is a cytokine, a chemokine, a lipokine, a myokine, a neurotransmitter, a neurotrophin, an interleukin, or an interferon. In certain embodiments that may be combined with the preceding embodiments, the protein is a hormone or growth factor. In certain embodiments the macromolecule is a hormone receptor or growth factor receptor. In certain embodiments the protein is a receptor or receptor domain. In certain embodiments the macromolecule is a receptor agonist or a receptor antagonist of the receptor or receptor domain. In certain embodiments that may be combined with the preceding embodiments, the protein is a neurotransmitter or neurotrophin. In certain embodiments the macromolecule is a neurotransmitter receptor or neurotrophin receptor.

In some embodiments, the invention further relates to computer code for determining SAP according to the methods of the invention. In other embodiments, the invention relates to a computer, a supercomputer, or cluster of computers dedicated to performing the methods of the invention. In yet other aspect, the invention provides a web-based, server based, or internet based service for determining aggregation prone regions on a protein, the service comprising accepting data about a protein (e.g., a protein structural model) from a user (e.g., over the internet) or retrieving such data from a database such that the service provider can generate, retrieve, or access a static structure of the protein, optionally including molecular dynamics modeling of the protein to provide a dynamic structure of the protein, determining SAP for atoms or residues of the protein based on the static or dynamic structure so generated, and returning the SAP data, for example, as a structural model mapped with said SAP data by the service provider, to a user. In some embodiments, the user is a person. In other embodiments the user is a computer system or automated computer algorithm In some embodiments the present invention proves an SAP calculation system comprising: a web server for providing a web service for calculating SAP to a user terminal through the Internet; a database for storing general information on the calculation method, amino acid hydrophobicity, etc., and a calculation server for performing the SAP calculation based on information in the database and information provided or transmitted through the internet by the user.

In some embodiments, the web server and the calculation server are the same computer system. In some embodiments the computer system is a supercomputer, a cluster computer, or a single workstation or server.

In a related embodiment the web server of the SAP calculation system further comprises a controller for controlling the entire operation, a network connection unit for connection to the Internet, and a web service unit for providing a web service for calculating SAP to the user terminal connected through the Internet.

In addition, embodiments of the present invention further relate to computer storage products with a computer readable medium that contain program code for performing various computer-implemented operations, e.g., calculating the SAP for a structural model, calculating SAA, calculating effective-SAA, manipulating structural models, implementing molecular dynamics simulations, organizing and storing relevant data, or performing other operations described herein. The computer-readable medium is any data storage device that can store data which can thereafter be read by a computer system. Examples of computer-readable media include, but are not limited to hard disks, floppy disks, flash drives, optical discs (e.g., CDs, DVDs, HD-DVDs, Blu-Ray discs, etc.) and specially configured hardware devices such as application-specific integrated circuits (ASICs) or programmable logic devices (PLDs). The computer-readable medium can also be distributed as a data signal embodied in a carrier wave over a network of coupled computer systems so that the computer-readable code is stored and executed in a distributed fashion. It will be appreciated by those skilled in the art that the above described hardware and software elements are of standard design and construction. The computer, internet, server, and service related embodiments described above may further apply to the SAA and the effective-SAA as well as SAP.

III. Pharmaceutical Compositions Containing Peptides and Peptide Variants of the Invention In another aspect, the present invention provides a composition, e.g., a pharmaceutical composition, containing one or more protein variants produced by the methods of the invention, formulated together with a pharmaceutically acceptable carrier. Pharmaceutical compositions of the invention also can be administered in combination therapy, i.e., combined with other agents. For example, the combination therapy can include a protein of the present invention combined with at least one other anti-cancer agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., the protein or variant thereof of the invention, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Exemplary formulations comprise at least one protein variant of the invention and can comprise lower concentrations of stabilizing (or disaggregation) agents which can, in addition to the methods disclosed herein, be used to prevent or diminish aggregation of a protein. Accordingly, conventional methods used to prevent aggregation may be employed in the development of pharmaceutical compositions containing protein variants produced by the methods of the present invention. For example, a variety of stabilizing or disaggregating compounds may be included in pharmaceutical compositions of the invention depending on their intended use and their biological toxicity. Such stabilizing compounds may include, for example, cyclodextrin and its derivatives (U.S. Pat. No. 5,730,969), alkylglycoside compositions (U.S. patent application Ser. No. 11/474,049), the use of chaperone molecules (e.g., LEA (Goyal et al., Biochem J. 2005, 388(Pt 1):151-7; the methods of U.S. Pat. No. 5,688,651), betaine compounds (Xiao, Burn, Tolbert, Bioconjug Chem. 2008 May 23), surfactants (e.g., Pluronic F127, Pluronic F68, Tween 20 (Wei et al. International Journal of Pharmaceutics. 2007, 338(1-2):125-132)), and the methods described in U.S. Pat. Nos. 5,696,090, 5,688,651, and 6,420,122 which are incorporated herein by reference.

Exemplary formulations also comprise a protein variant of the invention which exhibits an altered propensity for interaction with a binding partner together with a pharmaceutically acceptable carrier, adjuvant and/or excipient.

In addition, proteins, and in particular antibodies, are stabilized in formulations using combinations of different classes of excipients, e.g., (1) disaccharides (e.g. Saccharose, Trehalose) or polyols (e.g. Sorbitol, Mannitol) act as stabilizers by preferential exclusion and are also able to act as cryoprotectants during lyophilization, (2) surfactants (e.g. Polysorbat 80, Polysorbat 20) act by minimizing interactions of proteins on interfaces like liquid/ice, liquid/material-surface and/or liquid/air interfaces and (3) buffers (e.g. phosphate-, citrate-, histidine) help to control and maintain formulation pH. Accordingly, such disaccharides polyols, surfactants and buffers may be used in addition to the methods of the present invention to further stabilize proteins and prevent their aggregation.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the protein, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for a protein of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

Alternatively a protein of the invention can be administered as a sustained release formulation, in which case less frequent administration is required. Dosage and frequency vary depending on the half-life of the administered substance in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of protein of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for binding moieties of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, protein of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

EXAMPLES

Introduction to the Examples

Molecular simulation techniques for predicting aggregation prone regions and studying the mechanism of aggregation have mostly employed comparatively simple simulation models (Ma and Nussinov. *Curr. Opin. Chem. Biol.* 2006, 10, 445-452; Cellmer, et al., TRENDS in Biotechnology 2007, 25(6), 254) unlike the detailed atomistic models which may be employed in the present invention. The least detailed of the simulation models employed was the lattice model, which was used in numerous studies of protein aggregation (Harrison et al. J. MoL Biol. 1999, 286,593-606; Dima and Thirumalai. Protein Sci. 2002, 11, 1036-1049; Leonhard et al. Protein Sci. 2004, 13, 358-369; Patro and Przybycien. Biophys. J. 1994, 66, 1274-1289; Patro and Przybycien. Biophys. J. 1996, 70, 2888-2902; Broglia et al. Proc. Natl. Acad. Sci. U.S.A. 1998, 95, 12930-12933; Istrail et al. Comput. Biol. 1999, 6, 143-162; Giugliarelli et al. Chem. Phys. 2000, 113, 5072-5077; Bratko et al. J. Chem. Phys. 2001, 114, 561-569; Bratko and Blanch J. Chem. Phys. 2003, 118, 5185-5194; Combe and Frenkel Chem. Phys. 2003, 118, 9015-9022; Toma and Toma. Biomacromolecules 2000, 1, 232-238; Gupta et al. Protein Sci. 1998, 7, 2642-2652; and Nguyen and Hall Biotechnol. Bioeng. 2002, 80, 823-834). Here each residue is represented as a bead occupying a single site on a three dimensional lattice. Because of its simplicity, the lattice model is less computationally demanding and has been used to simulate large systems for long time scales. Although these lattice models provide insight into the basic physics underlying protein aggregation, they do not accurately represent the secondary and tertiary structure, and cannot adequately account for different atomistic level interactions such as hydrogen bonding.

A more detailed model compared to the lattice model is the intermediate resolution model in which a few atoms are usually combined into a single bead, and pseudo-bonds are sometimes introduced to maintain the backbone bond angles and isomerization states (Smith and Hall, Mol. Biol. 2001, 312, 187-202; Smith and Hall. Proteins: Struct., Funct., Genet. 2001, 44, 344-360; Smith and Hall. Proteins: Struct., Funct., Genet. 2001, 44, 376-391; Nguyen, et al., Protein Sci. 2004, 13, 2909-2924; Nguyen and Hall, Proc. Natl. Acad. Sci. U.S.A., 2004, 101(46), 16180-16185; Nguyen and Hall. J. Am. Chem. Soc., 2006, 128, 1890-1901; Jang, et al., Biophys. J. 2004, 86, 31-49; Jang, et al., Protein Sci. 2004, 13, 40-53). This model was successfully used to simulate the formation of fibrils from systems containing between 12 and 96 polyalanine peptides (16-residue each) starting from a random state (Nguyen and Hall, Proc. Natl. Acad. Sci. U.S.A., 2004, 101(46), 16180-16185; Nguyen and Hall, J. Am. Chem. Soc., 2006, 128, 1890-1901). Dokholyan and co-workers applied such a model to study the formation of fibrillar β-sheet structures by eight model Src SH3 domain proteins (Ding, et al., Mol. Biol. 2002, 324, 851-857) or by 28 model AP (1-40) peptides (Peng, et al., Phys. ReV. E: Stat. PhInterdiscip. Top. 2004, 69, 41908-41914.).

Unlike simpler models, atomistic models include all the atomistic details such as hydrogen bonding and are thus more accurate than the lattice or the intermediate resolution models. Such atomistic models have been used either with an explicit solvent, or with an implicit solvent where the solvent is treated as a continuum. The explicit model is more accurate than the implicit model, but is also more computationally demanding. Such an atomistic model with implicit solvent was used to study the early stages of aggregation of the heptapeptide GNNQQNY (SEQ ID NO: 1), which is a part of the yeast protein Sup35 (Gsponer, et al., Proc. Natl. Acad. Sci. U.S. Pat. No. 2,003,100, 5154-5159.). A similar model was used for the aggregation of Ab16-22 amyloid peptide (KLVFFAE (SEQ ID NO: 2)) into antiparallel b Sheets (Klimov and Thirumalai, Structure 2003, 11, 295-307). Dokholyan and coworkers (Khare, et al., *Proteins*. 2005, 61, 617-632) used an explicit atomistic model to investigate the ordered aggregation propensity along the sequence of the enzyme Cu, Zn superoxide dismutase (SOD1). They have decomposed the SOD1 sequence into overlapping heptapeptides and performed a large number of explicit water molecular dynamics simulations (each of 0.5 ns) of monomeric, dimeric and tetrameric segments. With this they identified the amyloidogenic regions in the SOD1 sequence to be: the two termini, the β-strands 4 and 7, and the two crossover loops.

A similar molecular dynamics simulation protocol was developed to obtain structural information on ordered β-aggregation of amyloidogenic polypeptides (Cecchini et al., *J Mol Biol.* 2006, 357, 1306-1321.). The procedure is based on the decomposition of a polypeptide chain into overlapping segments and equilibrium molecular dynamics (MD) simulations of a small number of copies of each segment. The β-aggregation propensity along the sequence of the Alzheimer's Aβ (1-42) peptide was found to be highly heterogeneous with a maximum at the segment V$_{12}$HHQKLVFFAA$_{22}$ (SEQ ID NO: 3) and minima at four turn-like dipeptides. Using this technique, the predicted change in the aggregation propensity of a double-point mutant of the N-terminal domain of the yeast prion Ura2p was verified in vitro using the thioflavin T binding assay. Such a procedure to decompose the polypeptide chain into overlapping segments would be extremely challenging for systems such as antibodies because of their huge size. Even an atomistic simulation of a single full antibody in explicit solvent is very computationally demanding because of the huge size of an antibody. Therefore, there does not appear to be full antibody atomistic simulation in the literature.

However, there have been atomistic simulations of small parts of the antibody, mostly for the Fab fragment (Noon, et al., PNAS. 2002, 99, 6466; Sinha and Smith-Gill, Cell Biochemistry and Biophysics. 2005, 43, 253). In the current work, atomistic simulations of a full antibody molecule with an explicit solvent were performed. Based on these simulations, the aggregation prone regions on the antibody were identified using the 'Spatial-Aggregation-Propensity' parameter described herein. These aggregation prone regions were then mutated to design antibodies with enhanced stability. The Examples described herein refer to particular embodiments of the invention.

Example 1: Molecular Dynamics Simulation Methodology

Molecular dynamics simulations were performed for a full antibody using an all atom model. The initial structure for simulation for the full antibody was obtained from the X-ray structures of individual Fab and Fc fragments. The X-ray structure of a proof-of-concept (POC) Fab fragment was selected for modeling onto the X-ray structure of Fc obtained from the IgG1 antibody 1HZH (Saphire et al., Science. 2001, 293, 1155). 1HZH was chosen since the X-ray structure is known for the full antibody and since the Fc structure is the same for all of the IgG1 class of antibodies. The structure of a full POC antibody was then obtained by aligning the Fab and Fc fragments using the 1HZH structure as a model template. In order to align the fragments at the correct distance and orientation, the RMSD (Root Mean Square Deviation) was minimized between the common CYS residues of the fragments and the full antibody template (1HZH). The CYS residues were chosen because each antibody sub-domain (cH1, cH2 etc.) contains a disulphide bond, and thus CYS residues are broadly distributed across the whole antibody structure. The resulting full antibody structure was then used to perform explicit atom simulations for 30 ns. A G0 glycosylation pattern was used for the simulations since this is the most common glycosylation pattern observed in antibodies.

The CHARMM simulation package (Brooks et al. J. Comput. Chem., 1983, 4, 187) was used for set-up and analysis, and the NAMD package (Phillips et al. Journal of Computational Chemistry. 2005, 26, 1781) for performing simulations. The CHARMM fully atomistic force field (MacKerell et al. J. Phys Chem. B. 1998, 102, 3586) was used for the protein and TIP3P (Jorgensen et al. *J. Chem. Phys.*, 1983, 79, 926) solvent model for water. The simulations were performed at 298K and 1 atm in the NPT ensemble. The parameters for the sugar groups involved in glycosylation of the Fc fragment were derived to be consistent with the CHARMM force field, following from the CSFF force field (Kuttel et al. J. Comput. Chem., 2002, 23, 1236). The protonation states of Histidine residues at pH-7 were chosen based on the spatial proximity of electronegative groups. The full antibody was solvated in an orthorhombic box since this minimizes the number of water molecules required and thus minimizes the computational time. Periodic boundary conditions were used in all 3 directions. A water solvation shell of 8 Å was used in each direction of the orthorhombic box. The resulting total system size was 202130 atoms. Sufficient ions were added to neutralize the total charge of the system. The charge neutrality is required by the Ewald summation technique employed to calculate the contribution of electrostatic interactions in the system.

After the antibody was solvated, the energy was initially minimized with SD (Steepest Descents) by fixing the protein to allow the water to relax around the protein. Then the restraints were removed and the structure was further minimized with SD and ABNR (Adopted Basis Newton-Raphson). The system was then slowly heated to room temperature with 5° C. increment every 0.5 ps using a less time step. The system was then equilibrated for 1ns before computing properties of interest from the simulation. The configurations were saved every 0.1 ps during the simulation for further statistical analysis.

Example 2: Calculation of the Spatial Aggregation Propensity (SAP)

In order to overcome the shortcomings of SAA, a new parameter was defined called 'Spatial-Aggregation-Propensity' as described above.

In this example the 'Spatial-Aggregation-Propensity' was calculated for spherical regions with radius R centered on every atom in the antibody described in Example 1. The value of Spatial-Aggregation-Propensity was thus evaluated with a 30 ns simulation average for the Fc-fragment of the antibody for two different radii of patches (R=5 Å, 10 Å) (One of skill in the art will appreciate various time steps for simulation may be chosen according to the computational resources available and the desired resolution of the result). In both cases it was noticed that the majority of values were negative, indicating that most exposed regions are hydrophilic. This was as expected since most of the exposed protein surface is usually hydrophilic. It was also observed that there are a few regions with positive peaks for Spatial-Aggregation-Propensity indicating high exposed hydrophobicity. Going from lower radii of patches (5 Å) to the higher radii (10 Å) eliminates some peaks, whereas some other peaks are enhanced. Some peaks were eliminated because in these regions a small hydrophobic patch (with less than 5 Å radius) is surrounded by hydrophilic patches; thus, averaging over 10 Å leads to an effective decrease in hydrophobicity for the region. Whereas in some other regions the Spatial-Aggregation-Propensity at R=10 Å is enhanced because of hydrophobic patches surrounding a similar hydrophobic patch.

Above, the Spatial-Aggregation-Propensity was calculated as an average during the 30 ns simulation run. The results calculated using the simulation were then compared to the Spatial-Aggregation-Propensity of just the X-ray structure, without molecular simulation. The Spatial-Aggregation-Propensity (X-ray) was similar to that of the simulation-averaged value, having peaks in the same locations but with differences in the magnitude of the peaks. The differences were higher with the larger radius of patch, R=10 Å. This is probably because the differences are additive when looking at larges patch sizes. These differences arise due to the changing surface exposure of the residues in the dynamic simulation run. Nevertheless, this comparison shows that a good initial estimate of Spatial-Aggregation-Propensity, especially for low radius of patch R, can be obtained from the X-ray structure itself.

The Spatial-Aggregation-Propensity values from the simulation for R=5 Å and 10 Å were mapped onto the antibody structure. In both cases, the antibody surface was colored according to the values of the Spatial-Aggregation-Propensity. Positive values of Spatial-Aggregation-Propensity (hydrophobic) are shown in gray or black while negative values (hydrophilic) are in lighter gray or white. The intensity of color is proportional to the magnitude of SES. Therefore a highly exposed hydrophobic patch would be deep black, and similarly a highly exposed hydrophilic will be brighter white. Also the structural representation of the antibody is based on the solvent accessible area for each residue. At both the radii used in the calculation of Spatial-Aggregation-Propensity (5 Å and 10 Å) it was observed that the surface is predominantly white indicating that the surface is mostly hydrophilic. This is again as expected since most of the protein surface is usually hydrophilic. However, a few black areas are noticeable, indicating exposed hydrophobic regions. The contrast between the black and white regions is more prominent at the higher radii of patch used in the calculation of SAP, R=10 Å. These black (hydrophobic) regions have excellent correlation with regions of the antibody known to interact with other proteins: a deep black region in the hinge region is where the Fc-receptor interacts, a black region in the Fc fragment is where protein A and protein G interact, and a black patch at the end of Fab fragment is where the antibody binds to antigens. Spatial-Aggregation-Propensity was plotted for R=5 Å and 10 Å respectively, wherein the same correlation of peaks with interacting regions may be observed. The protein interaction sites were obtained from X-ray structure of protein complexes, PDB entries 1T89, 1FC2, and 1FCC (Radaev, J. Biol. Chem. 2001, 276 (19) 16469; Deisenhofer et al. Hoppe-Seyler's Z Physiol Chem. 1978. 359, 975-985; Deisenhofer, J. Biochemistry. 1981, 20, 2361-2370; Sauer-Eriksson et al. Structure. 1995, 3, 265). The hydrophobic interactions correlate very well with the positive peaks and the hydrophilic interactions correlate well with the negative peaks. Therefore, the spatial-aggregation-propensity parameter can be used to predict the binding sites of proteins as well. In the few exceptions in which residues with low Spatial-Aggregation-Propensity (i.e. close to zero, either positive or negative) also interact, it was observed that the interactions are actually with the atoms of the main backbone chain itself, instead of with the side chains.

Apart from the black patches already shown to interact with other proteins, additional black patches on the antibody surface were identified. One patch at the bottom of Fc is significantly hydrophobic, but it is somewhat buried inside, with hydrophilic region on its borders. Similarly two patches are hydrophobic and solvent exposed, but they are facing into the interior of the antibody. These patches could still be potentially involved in interactions with other proteins if they are exposed due to significant conformational changes or unfolding of the antibody. All of the hydrophobic patches could also be observed at the smaller patch radius (R=5 Å), although with less contrast compared to the higher patch radius (R=10 Å).

The Spatial-Aggregation-Propensity (X-ray) values which are based on just the X-ray structure were also mapped onto the antibody surface, to compare them with the simulation averaged values. The black hydrophobic aggregation prone patches are quite similar between the Spatial-Aggregation-Propensity calculated either through simulation or using just the X-ray structure. There are of course some differences, such as the intensity of patches in the region where Protein A and G interact. Nevertheless, this comparison demonstrates that Spatial-Aggregation-Propensity (X-ray) based on just the X-ray structure can be used to obtain a good description of the distribution of hydrophobic patches on the surface. This is important since the atomistic simulation of a full antibody is computationally demanding. For proteins lacking an X-ray structural model, the same Spatial-Aggregation-Propensity parameter can be applied to the structure generated through homology modeling or ab-initio structure prediction. The homology structure was observed to be very similar to the X-ray structure, and its Spatial-Aggregation-Propensity values are also similar to the X-ray structure.

Thus Spatial-Aggregation-Propensity identifies the hydrophobic patches on the surface of the antibody. These patches could be natively exposed or exposed due to dynamic fluctuations or partial unfolding of the antibody. Some of these hydrophobic patches also correlate well with regions interacting with other proteins. In order to test if these hydrophobic patches predicted by Spatial-Aggregation-Propensity are involved in aggregation as well, mutations in these specific regions were performed to change the hydrophobic residues into hydrophilic residues. The resulting antibodies showed less aggregation behavior and improved stability. Apart from identifying aggregation prone residues, it was also observed that the SAP method correctly identifies the regions of the antibody prone to binding with other proteins. Therefore, the method could be broadly applied to all proteins to identify the aggregation prone regions or binding regions with other proteins.

Example 3: Selection of Antibody Sites for Stability Engineering

The sites to be engineered for enhanced antibody stability were selected on the basis of the SAP parameter. This spatial parameter accounts for (1) Solvent accessible area (SAA) of each residue, (2) the residue's hydrophobicity, and (3) the spatial contributions of all residues within a certain radius. In this example, the hydrophobic residues that correspond to the positive peaks in CH2 were changed to non-hydrophobic residues. It was expected that this would improve the overall protein stability. The two selected sites (A1 and A2) correspond to two very hydrophobic residues. An analysis was undertaken of substitutions of these residues with lysine, a very hydrophilic amino acid with a positively charged side chain. Variant A1 and Variant A2 differ from wild-type by single amino substitution.

Example 4: Expression and Purification of the Antibody Variants

Antibody variants were generated by site-directed mutagenesis. All constructs were confirmed by DNA sequencing. Plasmid DNA at the mg scale was purified from bacterial cultures and transiently transfected into HEK 293 cells. Antibody wild type and variants were purified from the tissue culture supernatant on a Protein A column and passed over a Q Sepharose column to remove negatively charged impurities. At pH 7.0 and below, the antibodies are positively charged and remain in the flow-through, while negatively charged impurities bind to the positively charged matrix of the Q Sepharose column. The solution with purified antibody was concentrated and buffer exchanged with 20 mM His buffer pH 6.5 to a final concentration of 150 mg/ml.

As a quality control, aliquots of the purified and concentrated samples were analyzed by SDS-PAGE and circular dichroism. Both reducing and non-reducing conditions were used for the protein gels. We also compared the secondary structure of wild type antibody and variant A1 by circular dichroism.

Example 5: Biophysical Characterization

The stability of Variant A1 was compared to wild type in an accelerated aggregation experiment. Samples at 150 mg/ml in 20 mM His buffer pH 6.5 were incubated at 58° C. for up to 24 hours. The incubation was stopped by diluting the sample to 10 mg/ml with 15 mM K-Phosphate buffer, pH 6.5, and the percent of aggregation was determined by SEC-HPLC. Aggregation was calculated as the areas sum of all non-monomeric peaks divided by the total area of all peaks. The average of 2-4 samples for each time point is shown. The aggregates for Variant A1 are as low as 80% of the aggregates for wild type. Thus, a single point mutation reduces aggregate formation by 20%.

Wild type and Variant A1 was compared by Differential Scanning Micro-calorimetry (DSC, Microcal). Full antibodies are multi-domain proteins. DSC analysis indicates different melting temperatures for different domains (Ionescu, R. M., et al., J Pharm Sci. 2008, 97(4): p. 1414-26; Mimura, Y., et al., J Biol Chem. 2001, 276(49): p. 45539-47.). The constant CH2 and CH3 domains of human IgG1 Fc have melting temperatures around 70° C. and 82° C., respectively, at neutral pH (Ionescu, R. M., et al., J Pharm Sci. 2008, 97(4): p. 1414-26; Mimura, Y., et al., Role of oligosaccharide residues of IgG1-Fc in Fc gamma RIIb binding. J Biol Chem, 2001. 276(49): p. 45539-47.). Depending on the sequence of the antibody variable domains, Fab fragments may have different melting temperatures with respect to CH2 and CH3. Antibody C contains a Fab domain with unfolding transition that falls between the transitions of CH2 and CH3. Thus, CH2 is the antibody domain with the lowest melting temperature.

Wild type and Variant A1 were analyzed at a concentration of 2 mg/ml in 15 mM His pH 6.5 buffer and a heating rate of 1.5 degrees per minute. The sample data were analyzed by subtraction of the reference data, normalization to the protein concentration and DSC cell volume, and interpolation of a cubic baseline. A comparison of the thermograms shows an increase of the CH2 melting transition in Variant A1 compared to wild type.

Analysis of Variant A2, also engineered for stability based on Spatial-aggregation-propensity values, recapitulates the findings for Variant A1.

In summary, the biophysical analyses of the engineered antibody variants demonstrated a reduced aggregation and an enhanced stability. The strong correlation between engineered sites, variant stability, and DSC profiles is evidence of the effectiveness of the methodology for stabilizing therapeutic proteins.

Example 6: Effective-SAA

It has been observed that the peaks in effective SAA (3 residue sum) may correlate with aggregation prone regions in a protein structure. Accordingly, the Effective-SAA may be used as a separate, albeit less powerful, method to identify aggregation prone regions of a protein. High effective SAA (3 residue sum) values indicate the most hydrophobic regions and low values indicate the most hydrophilic regions. Data on a test protein which has a tendency for aggregate formation was obtained from short molecular simulations of 1.2 ns (folded) and 1 ns (mis-folded). The effective SAA was plotted for residues of the protein and it was observed that there was good correlation between the peaks of the effective-SAA and mis-matches in the bonding network of the protein structure. This indicates that the effective-SAA was accurately identifying residues of the protein structure which encourage protein misfolding or aggregation. Several mutants of the test protein were made and at least one showed promising results in retaining a properly folded protein structure.

Example 7: Prediction of Protein Binding Regions Using SAP

The SAP method was used to predict protein binding sites. Binding regions were predicted for two different proteins: an IgG1 antibody and EGFR. An IgG1 antibody is well known to bind with proteins such as Fc-receptor, Protein-A and Protein-G. The EGFR binds with epidermal growth factor (EGF), transforming growth factor (TGFα) and also with itself to form a dimer. These binding regions for IgG1 antibody and EGFR were used as models to demonstrate the capability of the SAP tool in predicting the binding regions.

Molecular Simulation Methods

Molecular dynamics simulations were performed for a full IgG1 antibody using an all atom model with explicit solvent. The starting structure for simulation was obtained by attaching the X-ray structures of individual Fab and Fc fragments of the antibody. The X-ray structure of the Fab fragment was obtained from Novartis Pharma AG. The X-ray structure of Fc fragment was obtained from that of another IgG1 antibody of similar sequence, 1HZH (Saphire et al., Science. 2001, 293, 1155). The structure of a full antibody was then obtained by aligning the Fab and Fc fragments using 1HZH structure as a model template. This antibody structure was called antibody-A. In order to align the fragments at the correct distance and orientation, the RMSD (Root Mean Square Deviation) was minimized between the common CYS residues of the fragments and the full antibody template (1HZH). This structure was then used to perform explicit atom simulations for 30 ns. The CYS residues in the resulting antibody-A were all involved in disulphide bonds, including the ones in the hinge region. A G0 glycosylation pattern was used for the simulations since this is one of the most common glycosylation patterns observed in antibodies.

The CHARMM simulation package (Brooks et al. J. Comput. Chem., 1983, 4, 187) was used for set-up and analysis, and the NAMD package (Phillips et al. Journal of Computational Chemistry., 2005, 26, 1781) for performing simulations. The CHARMM fully atomistic force field (Phillips et al. Journal of Computational Chemistry. 2005, 26, 1781) was used for the protein and TIP3P (Jorgensen et al. J. Chem. Phys., 1983, 79, 926) solvent model for water. The simulations were performed at 298 K and 1 atm in the NPT ensemble. The parameters for the sugar groups involved in glycosylation of the Fc fragment were derived in consistence with the CHARMM force field, following from the CSFF force field (Kuttel et al. J. Comput. Chem., 2002, 23, 1236). The protonation states of histidine residues at pH-7 were decided based on the spatial proximity of electronegative groups. The full antibody was solvated in an orthorhombic box since this minimizes the number of water molecules required and thus minimizes the computational time required. Periodic boundary conditions were used in all 3 directions. A water solvation shell of 8 Å was used in each direction of the orthorhombic box. The resulting total system size was 202,130 atoms. It was observed that the orthorhombic box remained stable during the 30 ns simulation without any significant change in box dimensions on all three axes. The initial box dimensions were 161.9 Å, 145.4 Å and 83.2 Å, respectively, and they changed very little during the 30 ns simulation, ending at 161.2 Å, 144.7 Å and 82.8 Å respectively. The antibody did not rotate significantly during the 30 ns simulation, thereby maintaining the minimum distance between the antibody and its periodic images of more than 14 Å. Sufficient ions were added to neutralize the total charge of the system. The charge neutrality was required by the Ewald summation technique that was used to calculate contribution due to the electrostatic interactions.

After the antibody was solvated, the energy was initially minimized with SD (Steepest Descent) by fixing the protein to allow the water to relax around the protein. Then the restraints were removed and the structure was further minimized with SD and ABNR (Adopted Basis Newton-Raphson). The system was then slowly heated to room temperature with 5° C. increments every 0.5 ps using a 1 fs time step. The system was then equilibrated for 1 ns before beginning computation of the various properties from simulation. The configurations were saved every 0.1 ps during the simulation for further statistical analysis.

SAP Tool to Predict Binding Regions of an IgG1 Antibody

The SAP tool was applied to the protein configurations obtained from molecular simulations. For faster predictions in high throughput applications, the SAP tool can also be applied to the protein x-ray structure or homology derived structure, with a caveat that it might lead to a loss of accuracy. The SAP value for each atom in the protein was defined as follows, $$(\text{Spatial-aggregation-propensity}(SAP))_{atom\ i} = \sum_{\substack{Simulation \\ Average}} \left\{ \sum_{\substack{Residues\ with\ atleast \\ one\ side\ chain\ atom \\ within\ R\ from\ atom\ i}} \left( \frac{SAA\ of\ side\ chain\ atoms\ within\ radius\ R}{SAA\ of\ side\ chain\ atoms\ of\ fully\ exposed\ residue} \times \text{Atom hydrophobicity} \right) \right\}$$

Here,
1) SAA of side chain atoms within radius R is computed at each simulation snapshot
2) SAA of side chain of fully exposed residue (say for amino acid 'X') is obtained by calculating the SAA of side chains of the middle residue in the fully extended conformation of tripeptide 'Ala-X-Ala'.
3) Residue Hydrophobicity is obtained from the hydrophobicity scale of Black and Mould (S. D. Black and D. R. Mould, Anal. Biochem. 193, 72 (1991)). The scale is normalized such that glycine has a hydrophobicity of zero. Therefore, amino acids that are more hydrophobic than glycine are positive and less hydrophobic than glycine are negative on the hydrophobic scale.

SAP gives the dynamically exposed hydrophobicity of a certain patch centered at the given atom on the protein surface. SAP is calculated for spherical regions with radius R centered on every atom in the protein. This gives a unique SAP value for each atom. Then the SAP for a residue is obtained by averaging the SAP of all its constituent atoms. The SAP values were thus evaluated using R=10 Å for an IgG1 antibody, and the values were mapped onto the antibody surface using a color scale to indicate the SAP value within a range of −0.5 to +0.5. These SAP values were calculated by averaging over the 30 ns full antibody atomistic simulation. Note that the SAP value at each residue gives the total exposed hydrophobicity of a patch centered on that residue, and not just the hydrophobicity for a single residue. The hydrophobicity scale (S. D. Black and D. R. Mould, Anal. Biochem. 193, 72 (1991)) was also directly mapped onto the surface for comparison. When viewing the hydrophobic map, the hydrophobic regions appeared to be randomly distributed throughout the surface, and it would be difficult to pick a certain hydrophobic region to be more dominant compared to the other. However, upon examining the SAP map of the same structure, it was easy to spot the high SAP regions, which indicate dynamically exposed hydrophobic regions. It is thermodynamically unfavorable for these patches to be exposed to water because of their hydrophobic nature. Therefore, they could be involved in protein binding in order to reduce their solvent exposure. These high SAP regions were identified as '1' through '6'. Patches '1' and '6' were located in the Fab fragment, and patches '2' through '5' were located in the Fc fragment. Patches '1' to '3' were openly exposed and, therefore, could easily interact with other proteins. On the other hand, patches '4' to '6' were solvent accessible but facing into the protein, making it hard for them interact with other proteins unless they were more openly exposed due to unfolding.

Next, the correlation of high SAP regions that represent exposed hydrophobic patches with protein binding regions was tested. The binding regions of the antibody with Fc receptor, protein-A, and protein-G were mapped on top of the SAP values. The protein binding sites were obtained from X-ray structures of protein complexes, PDB entries 1T89, 1FC2, and 1FCC (S. Radaev, et al., J. Biol. Chem, 276 (19) 16469 (2001); Deisenhofer, J., et al. Hoppe-Seyler's Z. Physiol. Chem. 359, 975-985 (1978); Deisenhofer, J, Biochemistry 20, 2361-2370 (1981); Sauer-Eriksson A. E. et al, Structure, 3, 265 (1995)). A strong correlation was found between hydrophobic patches identified through SAP and protein binding regions. The antigen bound with the CDR loop region marked SAP patch '1', the Fc receptor binds with SAP patch '2', and protein-A and protein-G bind with SAP patch '3'. Furthermore, DeLano et al. (DeLano W. L., et al., Science 287, 1279 (2000)) showed that the region where protein-A and protein-G bind (SAP patch '3') is a consensus binding region that is dominant for binding random peptides selected in vitro for high affinity. Patch '3' is also known to bind with rheumatoid factor and neonatal Fc-receptor. Therefore, the hydrophobic accessibility of patch '3' as indicated through SAP makes it a favorable region to bind with numerous proteins. Quite remarkably, all 3 openly exposed patches (SAP patch '1' to '3') were involved in binding. The core of the patch is involved in hydrophobic interactions, whereas the fringes are involved in polar interactions.

SAP at R=10 Å was analyzed to find the broad hydrophobic patches involved in binding with other proteins. These patches can be explored in more detail using the SAP at higher resolution, i.e., at a lower radius of R used in the SAP calculation. Therefore, the SAP values were calculated at R=5 Å for the antibody. These SAP values were mapped onto the antibody surface. Here, the positive SAP values indicate dynamically exposed hydrophobic patches, whereas the negative SAP values indicate dynamically exposed hydrophilic patches. Regions binding with Fc-receptor, protein-A and protein-G were also identified. Similar to results with SAP at R=10 Å, the SAP at R=5 Å also showed strong correlation between protein binding regions and peaks in SAP values. The hydrophobic binding regions correlated well with the positive peaks, and the hydrophilic (polar) binding regions correlated well with the negative peaks. In the few exceptions in which residues with low SAP (i.e. close to zero, either positive or negative) also interacted, we observed that the interactions were actually with the atoms of the main backbone chain itself, instead of with the side chains.

SAP Predicts Both Binding Regions and Aggregation Prone Regions

It has been demonstrated that the peaks in SAP also correspond to regions that are prone to protein self-aggregation (Chennamsetty, N., et al. Design of therapeutic antibodies with enhanced stability (Submitted)). Aggregation is a major degradation pathway for therapeutic proteins leading to their loss of activity and potential immunogenicity. Mutations engineered on the peaks of SAP led to stable antibodies with less aggregation propensity (Chennamsetty, N., et al. Design of therapeutic antibodies with enhanced stability (Submitted)). The 8 mutants generated by changing the hydrophobic residues in SAP peaks to hydrophilic residues were A1 (L235K), A2 (I253K), A3 (L309K), A4 (L235K L309K), A5 (L234K L235K), A6 (L235S), A7 (V282K), and A8 (L235K V282K L309K). The mutants were then tested for their aggregation behavior using accelerated aggregation experiments under heat stress at 150 mg/ml. The SEC-HPLC (size-exclusion high-performance liquid chromatography) results showed monomer increase from 91% for wild type to 92-97% for the variants, indicating less aggregation propensity of the mutants. Therefore, the sites with high SAP also represent the regions of high aggregation propensity.

The SAP tool thus predicted both protein-binding regions and aggregation prone regions. A likely explanation is that protein aggregation is also a form of protein-protein binding, albeit within the proteins of same kind. Furthermore, it was shown that there is an overlap between some of the aggregation prone regions and protein binding regions. This overlap was evident from the residues L235 and I253 that are involved in both protein binding and aggregation. Similar SAP analysis and protein engineering was performed on another IgG1 antibody where it was shown that the aggregation prone regions overlap with protein binding regions (Chennamsetty, N., et al. Design of therapeutic antibodies with enhanced stability (Submitted)). In this case, the mutations were carried out in the CDR regions where the antibody binds to antigen. The resulting mutants in the CDR regions showed less aggregation propensity, but could not bind to antigen and lost their activity. Thus, there are common characteristics to protein binding and aggregation prone regions. This is in agreement with other computational predictions made from sequences that protein binding and aggregation prone regions overlap (Wang, X. et al., mAbs, 1, 1-14 (2009)). Thus, the dynamically exposed hydrophobic patches identified through SAP are involved in both protein binding and protein self-aggregation.

The overlap between protein binding sites and aggregation prone sites however, presents a new challenge in therapeutic protein design because aggregation needs to be prevented while preserving the protein binding necessary for its function. To resolve this challenge, the SAP analysis at higher resolution (at R=5 Å) can be used to locate and modify aggregation prone sites around the binding regions without disturbing protein binding. For example, using SAP analysis on the IgG1 antibody it was determined that sites I253, L309 and V282 are all part of a broad patch (SAP region '3') involved in aggregation (Chennamsetty, N., et al. Design of therapeutic antibodies with enhanced stability (Submitted)). Mutants involving sites L309 and V282 {A3 (L309K), A4 (L235K L309K), A7 (V282K), and A8 (L235K V282K L309K)} were designed, leaving out the site I253 that was involved in binding to protein-A. The resulting mutants showed less aggregation propensity while still binding to protein-A. Thus, SAP technology can be effectively used to design proteins with a lower aggregation propensity while preserving the protein binding capacity.

SAP Predicts Binding Regions of EGFR

In addition to antibodies, SAP analysis was performed on another protein called epidermal growth factor receptor (EGFR) to predict its binding regions. EGFR is a cell surface receptor activated by binding of specific ligands including epidermal growth factor receptor (EGF) and transforming growth factor β (TGFβ). EGFR overexpression or overactivity has been associated with a number of cancers such as lung cancer and brain cancer. EGFR also binds with itself to form dimers. An SAP analysis was performed on EGFR to see if the predicted binding regions coincide with the binding regions of EGF, TGFα, and with another EGFR in the dimeric form.

The SAP values evaluated for EGFR at R=10 Å were mapped onto the EGFR surface. These SAP values were calculated by performing the analysis directly on the X-ray structure of EGFR obtained from PDB entry 1IVO (Ogiso, H. et al., Cell, 110: 775-787 (2002)). The hydrophobicity scale (S. D. Black and D. R. Mould, Anal. Biochem. 193, 72 (1991)) was also mapped onto the EGFR surface for comparison. As seen earlier in the case of the antibody, the hydrophobic residues for EGFR were distributed throughout the surface, and it would be difficult to isolate the ones potentially involved in binding. However, it was relatively easier to spot the high SAP regions, which indicate spatially exposed hydrophobic regions. Two such major patches were identified and marked as '1' and '2'.

The known binding regions of EGFR with EGF, TGFα, and with another EGFR in the dimeric form were mapped on top of the SAP values. These protein binding sites were obtained from X-ray structures of protein complexes, PDB entries 1IVO and 1MOX (Ogiso, H., et al. Cell, 110: 775-787 (2002); Garrett, T. P. J., et al. Cell, 110: 763-773 (2002)). The mapping indicated a strong correlation between hydrophobic patches identified through SAP and protein binding regions. EGFR binds with EGF and TGFα in SAP patch '1' and another smaller patch. It also binds with another EGFR in SAP patch '2'. Thus, the two major SAP patches are both involved in binding. Again as in the case of antibody, the core of the patches is involved in hydrophobic interactions, whereas the fringes are involved in polar interactions. Thus, SAP accurately predicted the binding regions of EGFR.

CONCLUSIONS

A computational tool called SAP has been described, which provides a measure of dynamic exposure of hydrophobic patches that can be used to predict protein binding regions. Using two model proteins, an IgG1 antibody and EGFR, it was shown that SAP accurately predicts protein binding regions. In the case of the IgG1 antibody, the binding regions with Fc-receptor, protein-A and protein-G correlated well with SAP peaks. For EGFR, the binding regions with EGF, TGFβ, and with another EGFR correlated well with SAP peaks. Thus, SAP was shown to be accurate in predicting binding regions, and the importance of hydrophobically exposed patches for protein-protein binding was demonstrated. The same SAP analysis could be performed on other proteins as well to predict their binding regions. In addition, it has been shown that some of the protein binding regions overlap with aggregation prone regions. This presents a challenge for therapeutic protein design because unfavorable aggregation must be prevented while preserving the protein binding necessary for its function. It has been shown that this challenge can be overcome using SAP analysis followed by protein engineering. Using SAP, the sites near the binding site that are involved in aggregation can be detected and modified to decrease aggregation propensity while preserving binding. This was demonstrated using the IgG1 antibody where the aggregation prone regions near the protein-A binding sites were modified to decrease aggregation while preserving the binding capacity. Similar protein engineering based on SAP could be performed near the antigen binding regions to decrease aggregation propensity while preserving activity. Thus, the SAP tool described here could be used to design stable therapeutic proteins, while at the same time preserving their binding sites. The SAP tool could be also used to determine the yet unknown binding sites for numerous proteins coming out of structural genomics initiatives, thereby providing important clues to their function.

EQUIVALENTS

Those skilled in the art will recognize, or be able to ascertain using no more than routine experimentation, many equivalents to the specific embodiments of the invention described herein. Such equivalents are intended to be encompassed by the following claims.

---

---

We claim:

1. An in vitro method of making a protein variant which exhibits a reduced propensity for aggregation and/or an altered binding affinity for a macromolecule, comprising
   replacing or deleting at least one amino acid residue within an aggregation prone region and/or a molecular binding region in the protein by site directed mutagenesis, wherein the aggregation prone region and/or a molecular binding region is identified using Spatial-Aggregation-Propensity (SAP) scores, wherein the SAP for a particular atom in the protein is calculated by:
   (a) providing a computer-readable structural model of the protein;
   (b) mapping, onto the structural model of the protein the SAP, wherein the SAP is calculated for a particular atom by:
      (i) identifying one or more atoms or amino acid residues in a structural model representing the protein, wherein the one or more atoms are within a defined spatial region centered on or within 30 Å of the particular atom or the one or more amino acid residues have at least one atom within a defined spatial region centered on or within 30 Å of the particular atom;

(ii) calculating, for each of the one or more atoms in the defined spatial region, a ratio of the solvent accessible area (SAA) of each of the one or more atoms to the SAA of a corresponding atom in an identical residue which is fully exposed;

(iii) multiplying each ratio by the atom hydrophobicity of the one or more atoms; and, (iv) summing the products of step (iii), wherein the sum of the products of step (iii) consists of contributions from the one or more atoms within the defined spatial region;

whereby the sum is the SAP for the particular atom; and wherein, optionally, the SAP for the particular atom is calculated by conducting a computational molecular dynamics simulation on the computer-readable structural model of the protein prior to step (i) and repeating steps (i)-(iv), each time conducting a further molecular dynamics simulation at a plurality of time steps, thereby producing multiple sums as in step (iv), and calculating the average of the sums;

whereby the calculated average is the SAP for the particular atom; and (c) identifying a region within the protein having a plurality of atoms having a SAP that exceeds a set SAP threshold;

wherein the aggregation prone region and/or the molecular binding region comprises the amino acids comprising said plurality of atoms, and wherein, if the amino acid residue is replaced and the region is the aggregation prone region, it is replaced with an amino acid residue which is more hydrophilic, such that the propensity for aggregation of the variant is reduced.

2. The method of claim 1, wherein the defined spatial region is a sphere having a radius of between 1-30 Å.

3. The method of claim 2, wherein the radius is 5 Å.

4. The method of claim 1, wherein the molecular dynamics simulation is performed using a simulation package selected from the group consisting of ABINIT, AMBER, Ascalaph, CASTEP, CPMD, CHARMM, DL_POLY, FIREBALL, GROMACS, GROMOS, LAMMPS, MDynaMix, MOLDY, MOSCITO, NAMD, Newton-X, ProtoMol, PWscf, SIESTA, VASP, TINKER, YASARA, ORAC, and XMD.

5. The method of claim 1, where the identifying comprises plotting the SAP values; calculating, for peaks in the plot, the area under the curve (AUC); and identifying one or more protein regions with a positive AUC, wherein the aggregation prone region and/or the molecular binding region comprises the identified protein regions.

6. The method of claim 1, wherein at least two amino acid residues within the aggregation prone region and/or the molecular binding region are replaced.

7. The method of claim 1, wherein at least one residue is replaced within more than one aggregation prone regions and/or more than one molecular binding regions within the protein.

8. The method of claim 1, wherein the protein is selected from the group consisting of an antibody, a Fab fragment, a Fab' fragment, an Fd fragment, an Fv fragment, an $F(ab')_2$ fragment, and an Fc fragment.

* * * * *

SEQUENCE LISTING

```
<160> NUMBER OF SEQ ID NOS: 3

<210> SEQ ID NO 1
<211> LENGTH: 7
<212> TYPE: PRT
<213> ORGANISM: Saccharomyces cerevisiae

<400> SEQUENCE: 1

Gly Asn Asn Gln Gln Asn Tyr
1               5

<210> SEQ ID NO 2
<211> LENGTH: 7
<212> TYPE: PRT
<213> ORGANISM: Homo sapiens

<400> SEQUENCE: 2

Lys Leu Val Phe Phe Ala Glu
1               5

<210> SEQ ID NO 3
<211> LENGTH: 11
<212> TYPE: PRT
<213> ORGANISM: Homo sapiens

<400> SEQUENCE: 3

Val His His Gln Lys Leu Val Phe Phe Ala Ala
1               5                   10
```